United States Patent
Croci

[11] Patent Number: 5,955,474
[45] Date of Patent: Sep. 21, 1999

[54] USE OF NEUROTENSIN ANTAGONISTS FOR THE TREATMENT OF EDEMATOUS CONDITIONS

[75] Inventor: Tiziano Croci, Milan, Italy

[73] Assignee: Sanofi, Paris, France

[21] Appl. No.: 08/509,016

[22] Filed: Jul. 31, 1995

[30] Foreign Application Priority Data

Aug. 4, 1994 [FR] France .................... 94 09687

[51] Int. Cl.[6] .................................. A61K 31/47
[52] U.S. Cl. .......................................... 514/314
[58] Field of Search .............................. 514/314

[56] References Cited

U.S. PATENT DOCUMENTS

5,204,354  4/1993  Chakravarty et al. .

FOREIGN PATENT DOCUMENTS

| | | |
|---|---|---|
| 2 263 635 | 8/1993 | United Kingdom . |
| 2 263 636 | 8/1993 | United Kingdom . |
| 2 263 637 | 8/1993 | United Kingdom . |
| 2 263 638 | 8/1993 | United Kingdom . |
| 2 263 639 | 8/1993 | United Kingdom . |

OTHER PUBLICATIONS

Dubuc et al., *Br. J. Pharmacol.*, Jun. 1994, vol. 112, No. 2, 352–354.
Azzi et al., *Eur. J. Pharmacol.*, Apr. 1, 1994, vol. 255, No. 1–3, 167–174.
Vink et al., *Semin. Oncol.*, Sep. 1987, vol. 14, No. 3, 263–281.
Baranowska et al., *Neuroendocrinol. Lett.*, 1987, vol. 9.
Kivlighn et al., *Clin, Exp. Pharmacol. Physiol.*, Jun. 1990, vol. 17, No. 6, 401–412.
Rioux et al., *Neuropeptides*, Mar. 1985, vol. 6, No. 1, 1–12.

*Primary Examiner*—William R. A. Jarvis
*Attorney, Agent, or Firm*—Bacon & Thomas

[57] ABSTRACT

This invention relates to the treatment of edematous conditions in an animal by administering a neurotensin antagonist having diuretic activity.

2 Claims, No Drawings

USE OF NEUROTENSIN ANTAGONISTS FOR THE TREATMENT OF EDEMATOUS CONDITIONS

The present invention relates to a novel use of neurotensin inhibitors.

More particularly, the invention relates to the use of neurotensin antagonists for the preparation of drugs with a diuretic action.

Numerous responses are associated with the endogenous release of neurotensin, in both the central and peripheral nervous systems; studies have been devoted to the effects of neurotensin on the renal function, examples being Salah D. Kivlighn et al., Clin. Exp. Pharmacol. Physiol., 1990, 17, 401–412; and Regul. Pept., 1987, 18, 29–35. However, the results of these studies do not allow conclusions to be drawn regarding the actual role of neurotensin in the kidney.

The first mention of selective neurotensin antagonists was made in EP-A-477049, which describes variously substituted pyrazole-3-carboxylic acid amides with an activity on the central nervous system, the cardiovascular system and the gastrointestinal system.

Among the compounds described in said patent application, 2-{[1-(7-chloroquinolin-4-yl)-5-(2,6-dimethoxyphenyl)-1H-pyrazole-3-carbonyl]amino}adamantane-2-carboxylic acid, called SR 48692 in the literature, has proved particularly potent and selective (D. Gully et al., Proc. Natl. Acad. Sci., USA, 1993, 90, 65–69).

Another class of compounds with an even more potent activity as neurotensin antagonists is the family of the 1-naphthylpyrazole-3-carboxamides des- cribed in French patent application no. 93 12136 filed on Oct. 12, 1993, which is incorporated in the present patent application by way of reference.

Other compounds active as neurotensin antagonists have been described, but their selectivity is not comparable to that of the pyrazoles mentioned above (J. P. Maffrand, Drugs of the Future, 1993, 18, 1137– 1141). Such compounds are UK-73,093 (Snider R. M., Bioorg. Med. Chem. Lett., 1992, 2, 1535–40) of formula (A):

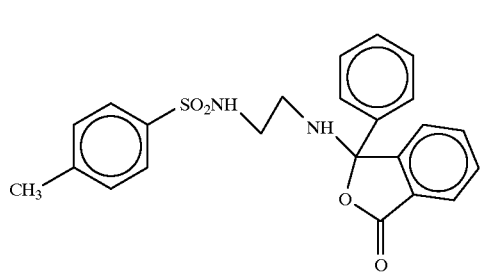

and those described in U.S. Pat. No. 5,204,354, GB 2263635, GB 2263636, GB 2263637, GB 2263638 and GB 2263639, incorporated therein by reference.

More recently, Kesten S. R. et al. (24th National Medicinal Chemistry Symposium, Salt Lake City, Utah, Jun. 21–25, 1994) have described a compound called PD-156425 of formula (B):

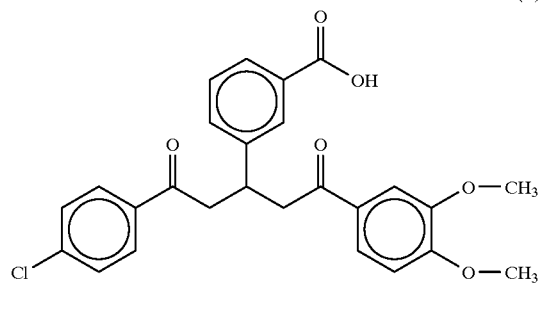

which is said to be capable of displacing [$^3$H]-neurotensin in rat brain preparations.

It has now been found, unexpectedly, that modulation of the activity of neurotensin by antagonistic compounds results in very substantial diuretic effects.

Thus, according to one of its features, the present invention relates to the use of neurotensin antagonists for the preparation of drugs with a diuretic action.

According to a preferred feature, the present invention relates to the use, for the preparation of drugs with a diuretic action, of pyrazole-3-carbox-amides of formulae (I), (I') and (I") below:

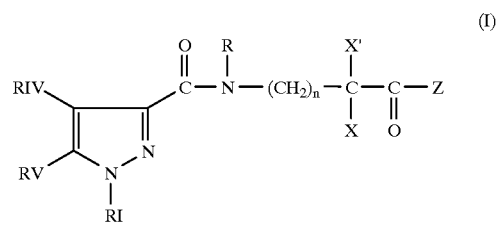

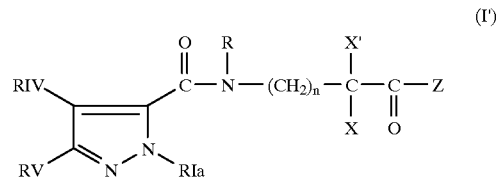

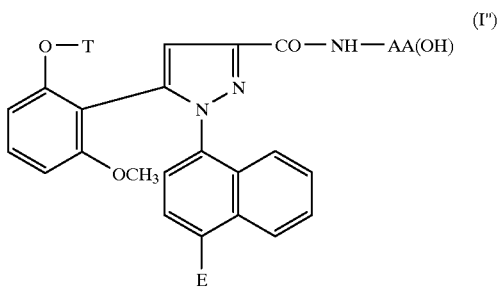

in which

RI is a group

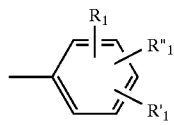

where $R_1$, $R'_1$ and $R''_1$ are each independently a hydrogen atom, a halogen atom, a hydroxyl, a linear or branched $C_1$–$C_4$-alkyl group, a $C_1$–$C_4$-alkoxy group, a trifluoromethyl group, a trifluoromethoxy group, a nitro group, a carboxyl group or an amino group;

a carboxyalkyl or alkoxycarbonylalkyl group in which the alkyls are $C_1$–$C_4$;

a cycloalkyl group in which the alkyls are $C_3$–$C_6$;

a tetrahydronaphthyl group;

a pyridyl group;

a naphthyl substituted by $R_1$, $R'_1$ and $R''_1$ as defined above;

a benzyl group substituted by $R_1$, $R'_1$ and $R''_1$ as defined above;

a cinnamyl group optionally substituted on the aromatic ring by a halogen, a hydroxyl or a $C_1$–$C_4$-alkoxy;

a quinolyl or isoquinolyl group optionally substituted by $R_1$, $R'_1$ and $R''_1$ as defined above;

a benzothiazol-2-yl group;

a quinoxalinyldione group;

a phthalazin-1-yl group;

a benzothiadiazolyl group; or a methylene group substituted by a 5- or 6-membered heterocyclic grouping such as, in particular, a pyridyl and a thienyl;

RIa is a benzyl group substituted by $R_1$, $R'_1$ and $R''_1$ as defined above;

R is hydrogen or a linear or branched $C_1$–$C_4$-alkyl;

n is 0, 1, 2 or 3;

either X is hydrogen and X' is hydrogen; a linear or branched $C_1$–$C_6$-alkyl; an aryl; a $C_1$–$C_4$-aminoalkyl; a $C_1$–$C_4$-hydroxyalkyl; a carboxyalkyl in which the alkyl group is $C_1$–$C_4$; an acetamidoalkylcysteine in which the alkyl group is $C_1$–$C_4$; a guanidinoalkyl in which the alkyl group is $C_1$–$C_4$; a nitroguanidinoalkyl in which the alkyl group is $C_1$–$C_4$; a $C_3$–$C_7$-cycloalkyl; an arylalkyl in which the alkyl is $C_1$–$C_4$ and in which the aryl is optionally substituted by a halogen, a hydroxyl or a $C_1$–$C_3$-alkyl; or a heteroarylalkyl in which the heteroaryl is an imidazolyl or an indolyl which is unsubstituted or substituted by a $C_1$–$C_4$-alkyl, a hydroxyl or a $C_1$–$C_4$-alkoxy, and in which the alkyl is $C_1$–$C_4$;

or if n is equal to zero, X is hydrogen and X' and

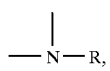

taken together, form a ring which is unsubstituted or substituted by a hydroxyl, of the formula

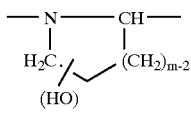

where m=2, 3 or 4 or a ring of the formula

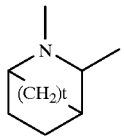

where t=1 or 2 or a ring of the formula

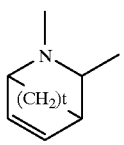

where t=1 or 2 or an indolinyl, perhydroindole or 4,5,6,7-tetrahydrothieno[2,3-c]pyrid-6-yl ring;

or X and X' are each independently a $C_1$–$C_4$-alkyl; a $C_3$–$C_6$-cycloalkyl; or a phenyl;

or X and X' are bonded together to form a cycloalkyl group having 2 to 12 carbon atoms, optionally substituted by a $C_1$–$C_3$-alkyl;

or X, X' and the carbon atom to which they are bonded form an adamantyl group; an adamantyl group substituted by one or two methyl groups, a hydroxyl, a $C_1$–$C_3$-alkoxy or a halogen atom; a 1-azaadamantyl group; a quinuclidinyl group; a piperidin-4-yl group optionally N-substituted by a benzyl group; a 2,2,6,6-tetramethylpiperidinyl group; a tetrahydronaphthyl group; a tetrahydropyran-4-yl or tetrahydrothiopyran-4-yl group; a 2,3-dihydro(4H)benzopyran-4-yl group; a 2,3-dihydro(4H)benzothiopyran-4-yl group; a group of formula a:

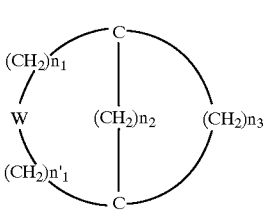

a in which $n_1$=0 or 1, $n'_1$=1 or 2, $n_2$=1, $n_3$=2 or 3 and W is a carbon atom or an oxygen atom, this group being bonded to

and to —C(O)—Z, as defined above, by a carbon atom of one or other of the rings; a group of formula b:

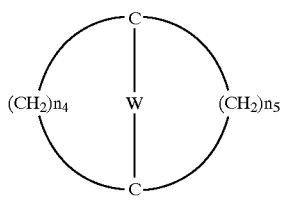

in which $n_4=2$, 3 or 4, $n_5=2$ or 3 and W is a carbon or oxygen atom, this group being bonded to

and to —C(O)—Z, as defined above, by a carbon atom of one or other of the rings, it optionally being possible for the rings of the groups a and b above to be substituted on one or other or both of the rings by one or two $C_1$–$C_4$-alkyl groups and it being impossible for the amino acid to be in the alpha-position of W if W is oxygen; a bicyclo[2,2,1]hept-5-en-2-yl group; an 8-oxabicyclo[3,2,1]oct-6-en-3-yl group; or an 8-thiabicyclo[3,2,1]octan-3-yl group;

or X is hydrogen and X' is an adamantyl group; an adamantyl group substituted by one or two methyls, a hydroxyl, a $C_1$–$C_3$-alkoxy or a halogen atom; a 1-azaadamantyl group; or a group of formula a or b as defined above, it being impossible for the bond between these rings and the carbon carrying —COZ and —N—R to be in the alpha-position of W if the latter is oxygen;

Z is a hydroxyl group; a $C_1$–$C_6$-alkoxy group; an oxygen atom substituted by a protecting group for carboxylic acids, such as a tert-butyl, a benzyl or a benzyl substituted by a halogen atom, a $C_1$–$C_6$-alkyl, a trifluoromethyl, a trifluoromethoxy or a carboxyl group; an amino group; or a nitrogen atom substituted by a carboxyalkyl in which the alkyl is $C_1$–$C_6$ and linear or branched, with the limitation that if Z is a substituted nitrogen atom as defined above and if n=0, then, when X=H, X' cannot be a group

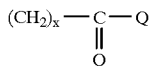

in which x=1 or 2 and Q is a hydroxyl, an amino which is free or substituted by a $C_1$–$C_6$-dialkyl, or a $C_1$–$C_6$-alkoxy;

RIV is a hydrogen atom, a halogen atom or a $C_1$–$C_6$-alkyl;

RV is
a group

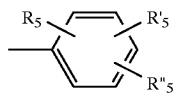

where $R_5$, $R'_5$ and $R''_5$ are each independently a hydrogen atom, a halogen atom, a linear or branched $C_1$–$C_4$-alkyl, a hydroxyl, a $C_1$–$C_4$-alkoxy, a nitro, a trifluoromethyl, a trifluoromethoxy, a cyano, an amino, a carboxyl, a $C_1$–$C_4$-carboxyalkyl or a phenyl;

a naphthyl group which is unsubstituted or substituted by a $C_1$–$C_4$-alkyl;

a pyridyl group; or a styryl group which is unsubstituted or substituted by a $C_1$–$C_4$-alkyl;

or RIV and RV, taken together, are a group

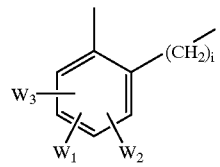

in which the phenyl group substitutes the pyrazole in the 5-position and the group -$(CH_2)i$—, in which i=1 to 3, substitutes the pyrazole in the 4-position, and $W_1$, $W_2$ and $W_3$ substitute the benzene ring and are independently hydrogen, a halogen or a hydroxyl group;

E is a group selected from —CN, —C($NH_2$)=N—OH, —$CONG_1G_2$, —CON($G_1$)($CH_2$)$_p$$NG'_1G'_2$, —O($CH_2$)$_q$$NG_1G_2$, —O($CH_2$)$_q$$CONG_1G_2$, —O($CH_2$)$_q$$COOG_1$, —O($CH_2$)$_q$$SO_2NG_1G_2$, —$NHCOG_3$, —NHCO($CH_2$)$_q$$NG_1G_2$, —$CH_2CONG_1G_2$, —$CH_2$CON($G_1$)($CH_2$)$_p$$NG'_1G'_2$, —$CH_2COOG_1$, —$CH_2NHCOG_3$, —$SO_2NG_1G_2$, —$NHSO_2G_1$, —$SO_2$N($G_1$)($CH_2$)$_q$$NG'_1G'_2$ and

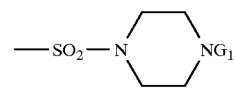

p=2 to 6;

q=1 to 6;

$G_1$, $G_2$, $G'_1$ and $G'_2$ are each independently a hydrogen or a $C_1$–$C_4$-alkyl or $G_1$ and $G_2$ or, respectively, $G'_1$ and $G'_2$, together with the nitrogen atom to which they are bonded, are a heterocycle selected from pyrrolidine, piperidine, piperazine, morpholine and thiomorpholine;

$G_3$ is hydrogen or a group selected from $C_1$–$C_8$-alkyl groups, $C_3$–$C_8$-cycloalkyl or -cycloalkylalkyl groups and $C_6$–$C_8$-aryl or -arylalkyl groups;

T is hydrogen, a $C_1$–$C_4$-alkyl, an allyl, a $C_3$–$C_8$-cycloalkyl, a ($C_3$–$C_8$)cycloalkylmethyl or a methoxyethyl; and the group —NH—AA(OH) is the amino acid residue

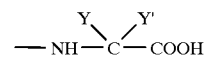

where Y is hydrogen and Y'0 is hydrogen, a $C_1$–$C_5$-alkyl or a non-aromatic $C_3$–$C_{15}$ carbocyclic radical, or Y and Y', together with the carbon atom to which they are bonded, form a non-aromatic $C_3$–$C_{15}$ carbocycle;

or a salt thereof, where appropriate, with pharmaceutically acceptable organic or mineral acids or with pharmaceutically acceptable mineral or organic bases.

Non-aromatic $C_3$–$C_{15}$ carbocycle is understood as meaning saturated or unsaturated, fused or bridged monocyclic or polycyclic radicals, which may be terpene radicals. These radicals are optionally monosubstituted or polysubstituted by a $C_1$–$C_4$-alkyl.

A particularly advantageous class of compounds of formula (I) above is that represented by the compounds of formula (II):

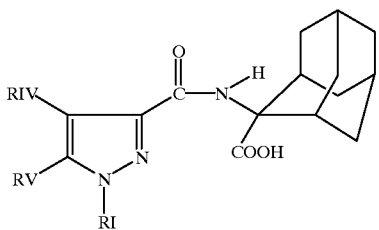

(II)

in which RI, RIV and RV are as defined above, and by the pharmaceutically acceptable salts and solvates thereof.

The preferred compounds among those of formula (II) above are 2-{[1-(7-chloroquinolin-4-yl)-5-(2,6-dimethoxyphenyl)-1H-pyrazole-3-carbonyl]amino}adamantane-2-carboxylic acid (SR 48692) and the pharmaceutically acceptable salts and solvates thereof.

Another advantageous class is represented by the compounds of formula (III):

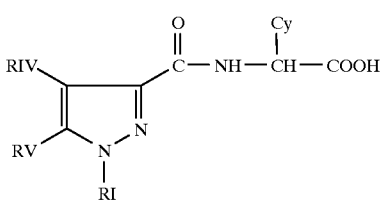

(III)

in which RI, RIV and RV are as defined above and Cy is a cycloalkyl having 3 to 8 carbon atoms, preferably cyclohexyl, and by the pharmaceutically acceptable salts and solvates thereof.

Another advantageous class is represented by the compounds of formulae (A) and (B) above and by the compounds described in U.S. Pat. No. 5,204,354, GB 2263635, GB 2263636, GB 2263637, GB 2263638 and GB 2263639, which have the following formulae (C), (D), (E), (F), (G) and (H):

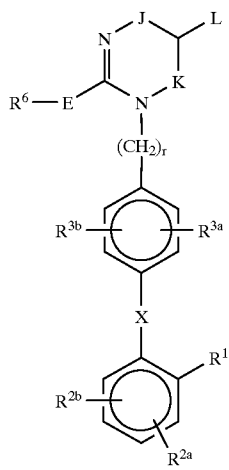

(C)

or a pharmaceutically acceptable salt thereof, wherein:
L is connected with J or K to form an aromatic ring as defined below;
J is —C(=M)— or J and L are connected together to form a 6 carbon aromatic ring substituted with $R^{7a}$, $R^{7b}$, $R^{8a}$ and $R^{8b}$;
K is —C(=M)— or K and L are connected together to form a 6 carbon aromatic ring substituted with $R^{7a}$, $R^{7b}$, $R^{8a}$ and $R^{8b}$, provided that only one of J and K is —C(=M)—; M is O or $NR^{22}$;
$R^1$ is
(a) —$NHSO_2R^{23}$,
(b) —$NHSO_2NHCOR^{23}$,
(c) —$NHCONHSO_2R^{23}$,
(d) —$SO_2NHR^{23}$,
(e) —$SO_2NHCOR^{23}$,
(f) —$SO_2NHCONR^4R^{23}$,
(g) —$SO_2NHCOOR^{23}$,
(h) —$SO_2NHOR^{23}$,
(i) —$CH_2SO_2NHCOR^{23}$,
(j) —$CH_2SO_2NHCONHR^{23}$,
(k) —$CO_2H$, or
(l) —1H-tetrazol-5-yl;
$R^{2a}$ and $R^{2b}$ are each independently
(a) H,
(b) Cl, Br, I, F,
(c) $CF_3$,
(d) $C_1$–$C_6$-alkyl,
(e) $C_1$–$C_6$-alkoxy,
(f) $C_1$–$C_6$-alkyl-S—,
(g) $C_2$–$C_6$-alkenyl,
(h) $C_2$–$C_6$-alkynyl,
(i) $C_3$–$C_7$-cycloalkyl,
(j) aryl, or
(k) aryl-$C_1$–$C_6$-alkyl;
$R^{3a}$ is
(a) H,
(b) Cl, Br, I, F,
(c) $C_1$–$C_6$-alkyl,
(d) $C_1$–$C_6$-alkoxy, or
(e) $C_1$–$C_6$-alkoxyalkyl;
$R^{3b}$ is
(a) H,
(b) Cl, Br, I, F,
(c) $C_1$–$C_6$-alkyl, (d) $C_3$–$C_7$-cycloalkyl,
(e) $C_1$–$C_6$-alkoxy,
(f) $CF_3$,
(g) $C_2$–$C_6$-alkenyl, or
(h) $C_2$–$C_6$-alkynyl;

$R^4$ is
(a) H,
(b) $C_1$–$C_6$-alkyl,
(c) aryl, wherein aryl is phenyl or naphthyl, either unsubstituted or substituted with one or two substituents selected from the group consisting of halogen, $N(R^4)_2$, $CO_2R^4$, $C_1$–$C_4$-alkyl, $C_1$–$C_4$- alkoxy, $NO_2$, $CF_3$, $C_1$–$C_4$-alkylthio, and OH,
(d) aryl-$C_1$–$C_6$-alkyl, or
(e) heteroaryl, wherein heteroaryl is an unsubstituted, monosubstituted or disubstituted five or six membered aromatic ring selected from thiazole, imidazole, pyrazole, oxazole, pyridine, thiazine, pyrazine, pyrimidine wherein the substituents are members selected from the group consisting of —OH, —SH, —$C_1$–$C_4$-alkyl, —$C_1$–$C_4$- alkoxy, —$CF_3$, Cl, Br, F, I, -$NO_2$, —$CO_2$H, —$CO_2$—($C_1$–$C_4$-alkyl), —$NH_2$, —$NH(C_1$–$C_4$-alkyl) and —$N(C_1$–$C_4$-alkyl)$_2$;

E is a single bond, —$NR^{13}(CH_2)_s$—, —$S(O)_x(CH_2)_s$— where x is 0 to 2 and s is 0 to 5, —CH(OH)—, —O—, or —CO—; p1 $R^6$ is
(a) H,
(b) aryl,
(c) $C_1$–$C_6$-alkyl, $C_2$–$C_5$-alkenyl or $C_2$–$C_5$-alkynyl each of which is unsubstituted or substituted with a substituent selected from the group consisting of aryl, Cl, Br, I, F, $C_3$–$C_7$-cycloalkyl, —$NH_2$, —NH($C_1$–$C_4$-alkyl), —$OR^4$, —$N(C_1$–$C_4$-alkyl)$_2$, —NH—$SO_2R^4$, —$COOR^4$, and —$SO_2NHR^9$,
(d) heteroaryl, or
(e) $C_3$–$C_7$-cycloalkyl;

$R^{7a}$ and $R^{7b}$ are independently
(a) H,
(b) $C_1$–$C_6$-alkyl, $C_2$–$C_6$-alkenyl or $C_2$–$C_6$-alkynyl,
(c) Cl, Br, I, F,
(d) $CF_3$,
(e) when $R^{7a}$ and $R^{7b}$ are bonded to adjacent carbon atoms, they joined to form a phenyl ring, or
(f) aryl;

$R^{8a}$ and $R^{8b}$ are independently
(a) H,
(b) $C_1$–$C_6$-alkyl, unsubstituted or substituted with a substituent selected from the group consisting of —OH, -guanidino, $C_1$–$C_4$-alkoxy, —$N(R^4)_2$, $COOR^4$, —$CON(R^4)_2$, —O—$COR^4$, -aryl, -heteroaryl, —$S(O)_x$—$R^{23}$, -tetrazol-5-yl, —$CONHSO_2R^{23}$, —$SO_2NH$— heteroaryl, —$SO_2NHCOR^{23}$, —$PO(OR^4)_2$, —$PO(OR^4)R^9$, —$SO_2NH$-CN, —$NR^{10}COOR^{23}$, morpholino, N—($C_1$–$C_6$- alkyl)piperazine, and —$COR^4$,
(c) —CO-aryl,
(d) —$C_3$–$_7$-cycloalkyl,
(e) Cl, Br, I, F,
(f) —OH,
(g) —$OR^{23}$,
(h) —$C_1$–$C_4$-perfluoroalkyl,
(i) —$S(O)_x$—$R^{23}$,
(j) —$COOR^4$,
(k) —$SO_3H$,
(l) —$NR^4R^{23}$,
(m) —$NR^4COR^{23}$,
(n) —$NR^4COOR^{23}$,
(o) —$SO_2NR^9R^{10}$,
(p) —$NO_2$,
(q) —$NR^4SO_2R^{23}$,
(r) —$NR^4CONR^4R^{23}$,
(s)

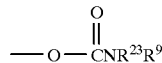

(t) -aryl or -heteroaryl as defined above,
(u) —$NHSO_2CF_3$,
(v) —$SO_2NH$-heteroaryl,
(w) —$SO_2NHCOR^{23}$,
(x) —$CONHSO_2R^{23}$,
(y) —$PO(OR^4)_2$,
(z) —$PO(OR^4)R^9$,
(aa) -tetrazol-5-yl,
(bb) —CONH(tetrazol-5-yl),
(cc) —$COR^4$,
(dd) —$SO_2NHCN$,
(ee)

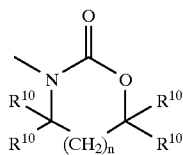

where n=0 or 1,
(ff) —CO-heteroaryl,
(gg) —$NR^4SO_2NR^{23}R^9$,
(hh) —$N[CH_2CH_2]_2NR^{24}$, wherein $R^{24}$ is $C_1$–$C_6$-alkyl, —$C_3$–$C_7$-cycloalkyl, —$CONR^9R^{10}$, -heteroaryl, -phenyl, —CO—$C_3$–$C_7$-cycloalkyl, —CO—$C_1$–$C_6$-alkyl, —$SO_2$—$C_1$–$C_6$-alkyl, or —$SO_2$—$C_3$–$C_7$-cycloalkyl, or
(ii) —$N[CH_2CH_2]_2O$;

$R^9$ is H, $C_1$–$C_5$-alkyl, aryl or arylmethyl;

$R^{10}$ is H, $C_1$–$C_4$-alkyl;

$R^{11}$ is H, $C_1$–$C_6$-alkyl, $C_1$–$C_4$-alkenyl, $C_1$–$C_4$-alkoxyalkyl, or

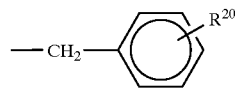

$R^{12}$ is —CN, —$NO_2$, —$CF_3$ or —$CO_2R^4$;

$R^{13}$ is H, ($C_1$–$C_4$-alkyl)CO—, $C_1$–$C_6$-alkyl, allyl, $C_3$–$C_6$-cycloalkyl, aryl or arylmethyl;

$R^{14}$ is H, $C_1$–$C_8$-alkyl, $C_1$–$C_8$-perfluoroalkyl, $C_3$–$C_6$-cycloalkyl, aryl or arylmethyl; p1 $R^{15}$ is H, $C_1$–$C_6$-alkyl;

$R^{16}$ is H, $C_1$–$C_6$-alkyl, $C_3$–$C_6$-cycloalkyl, aryl or arylmethyl;

$R^{17}$ is —$NR^9R^{10}$, —$OR^{10}$, —$NHCONH_2$, —$NHCSNH_2$,

 or

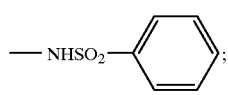 ;

$R^{18}$ and $R^{19}$ are independently $C_1$–$C_4$-alkyl or taken together are —$(CH_2)_q$— where q is 2 or 3;

$R^{20}$ is H, —$NO_2$, —$H_2$, —OH or —$OCH_3$;

$R^{21}$ is H, aryl, or $C_1$–$C_4$-alkyl optionally substituted with aryl, —$NH_2$, —$NH(C_1$–$C_4$-alkyl), —$N(C_1$–$C_4$-alkyl)$_2$, —$CO_2R^4$, —OH, —$SO_3H$, or —$SO_2NH_2$;

$R^{22}$ is
(a) aryl,
(b) heteroaryl,
(c) $C_1$–$C_6$-alkyl unsubstituted or substituted with a substituent selected from the group consisting of aryl, heteroaryl, —OH, —$NH_2$, —$NH(C_1$–$C_4$-alkyl), —$N(C_1$–$C_4$-alkyl)$_2$, —$CO_2R^4$, Cl, Br, F, I, and —$CF_3$, or
(d) perfluoro-$C_1$–$C_4$-alkyl;

$R^{23}$ is
(a) aryl,
(b) heteroaryl,
(c) $C_3$–$C_7$-cycloalkyl,
(d) $C_1$–$C_8$-alkyl wherein alkyl is unsubstituted or substituted with one or two substituents selected from the group consisting of aryl, heteroaryl, —OH, —SH, $C_1$–$C_4$-alkyl, —$O(C_1$–$C_4$-alkyl), —$S(C_1$–$C_4$-alkyl), —$CF_3$, Cl, Br, F, I, —$NO_2$, —$CO_2H$, —$CO_2$–$C_1$–$C_4$-alkyl, —$NH_2$, —$NR^4CO_2R^{22}$, —$NH(C_1$–$C_4$-alkyl), —$N(C_1$–$C_4$-alkyl)$_2$, —$PO_3H_2$, —$PO(OH)(O$–$C_1$–$C_4$-alkyl), —$PO(OR^4)R^9$, —$NR^4COR^{22}$, —$CONR^4R^{22}$, —$OCONR^4R^{22}$, —$SO_2NR^4R^{22}$, or —$NR^4SO_2R^{22}$, or
(e) perfluoro-$C_1$–$C_4$-alkyl;

X is
(a) a carbon-carbon single bond,
(b) —CO—,
(c) —O—,
(d) —S—,
(e) 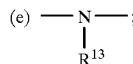 ;
(f) 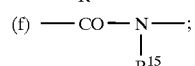 ;
(g) 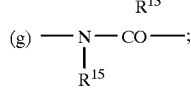 ;
(h) —$OCH_2$—,
(i) —$CH_2O$—,
(j) —$SCH_2$—,
(k) —$CH_2S$—,
(l) —$NHC(R^9)(R^{10})$,
(m) —$NR^9SO_2$—,
(n) —$SO_2NR^9$—,
(o) —$C(R^9)(R^{10})NH$—,
(p) —CH=CH—,
(q) —CF=CF—,
(r) —CH=CF—,
(s) —CF=CH—,
(t) —$CH_2CH_2$—,
(u) —$CF_2CF_2$—, (v) 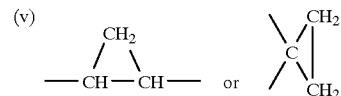

(w) 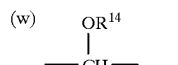

(x) 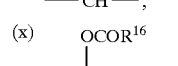

(y) 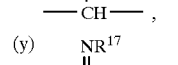

(z) 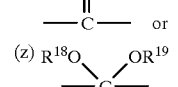 , r is 1 or 2.

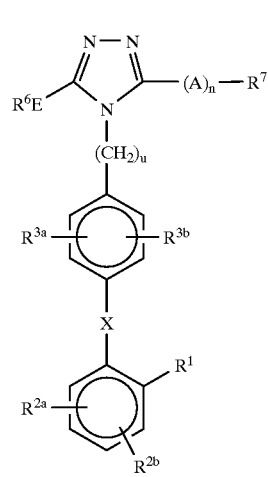

(D)

or a pharmaceutically acceptable salt thereof, wherein:

$R^1$ is
(a) —$NHSO_2R^{23}$,
(b) —$NHSO_2NHCOR^{23}$,
(c) —$NHCONHSO_2R^{23}$,
(d) —$SO_2NHR^{23}$,
(e) —$SO_2$—$NHCOR^{23}$,
(f) —$SO_2NHCONR^9R^{23}$,
(g) —$SO_2NHCOOR^{23}$,
(h) —$SO_2NHOR^{23}$,
(i) —$CH_2SO_2NHCOR^{23}$,
(j) —$CH_2SO_2NHCONHR^{23}$,
(k) —$CO_2H$, or
(l) —1H-tetrazol-5-yl;

$R^{2a}$ and $R^{2b}$ are each independently:
(a) hydrogen,
(b) Cl, Br, I, F,
(c) $CF_3$,
(d) $C_1$–$C_4$-alkyl, or
(e) $C_1$–$C_4$-alkoxy;

$R^3a$ is
(a) H,
(b) Cl, Br, I, F,
(c) $C_1$–$C_6$-alkyl, (d) $C_1$–$C_6$-alkoxy, or
(e) $C_1$–$C_6$-alkoxy-$C_1$–$C_4$-alkyl;

$R^3b$ is
(a) H,
(b) Cl, Br, I, F,
(c) $C_1$–$C_6$-alkyl,
(d) $C_3$–$C_6$-cycloalkyl,
(e) $C_1$–$C_6$-alkoxy, or
(f) $CF_3$;

$R^4$ is H, $C_1$–$C_6$ alkyl, benzyl or phenyl;

$R^5$ is H or

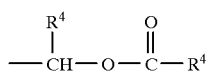

E is a single bond, —$NR^{13}(CH_2)_s$—, —$S(O)_x(CH_2)_s$— where x is 0 to 2 and s is 0 to 5, —CH(OH)—, —$O(CH_2)_s$—, —CO—;

$R^6$ is
(a) aryl, wherein aryl is defined as phenyl or naphthyl which can be unsubstituted or substituted with 1 or 2 substituents selected from the group consisting of Cl, Br, I, F, —O—$C_1$–$C_4$- alkyl, $C_1$–$C_4$-alkyl, —$NO_2$, —$CF_3$, —$SO_2NR^9R^{10}$, —S—$C_1$–$C_4$-alkyl, —OH, —$NH_2$, $C_3$–$C_7$-cycloalkyl, $C_2$–$C_{10}$-alkenyl;
(b) $C_1$–$C_6$-alkyl, $C_2$–$C_6$-alkenyl or $C_2$–$C_6$-alkynyl each of which can be optionally substituted with a substituent selected from the group consisting of aryl as defined above, —O— $C_1$–$C_4$-alkyl, $C_3$–$C_7$-cycloalkyl, Cl, Br, I, F, —OH, —$NH_2$, —NH($C_1$–$C_4$-alkyl), —N($C_1$–$C_4$-alkyl)$_2$, —NH—$SO_2R^4$, —$COOR^4$, —$SO_2NHR^9$, —S—$C_1$–$C_4$-alkyl;
(c) an unsubstituted, monosubstituted or disubstituted aromatic 5 or 6 membered ring which can contain one or two members selected from the group consisting of N, O, S, and wherein the substituents are members selected from the group consisting of —OH, —SH, $C_1$–$C_4$-alkyl, $C_1$–$C_4$-alkyloxy, —$CF_3$, Cl, Br, I, F, or $NO_2$;
(d) mono-, di-, tri- or perfluoro-$C_1$-$C_5$-alkyl;
(e) $C_3$-$C_7$-cycloalkyl, unsubstituted or substituted with one or more substituents selected from the group consisting of $C_1$–$C_4$-alkyl, —O—$C_1$–$C_4$-alkyl, —S—$C_1$–$C_4$-alkyl, —OH, perfluoro-$C_1$–$C_4$-alkyl or Cl, Br, F, I;
(f) $C_3$–$C_7$-cycloalkyl-$C_1$–$C_3$-alkyl wherein the cycloalkyl is substituted as in (e) above;

A is $S(O)_p$, —O—NHC(=O)—, —C(=O)$NR^{13}$—, or —$NR^{13}$—, wherein p is 0 to 2;

$R^7$ is
(a) $C_1$–$C_{10}$-alkyl;
(b) substituted $C_1$–$C_{10}$ alkyl in which one or more substituent(s) is selected from
(1) Cl, Br, I, F,
(2) hydroxy,
(3) $C_1$–$C_{10}$-alkoxy,
(4) $C_1$–$C_5$-alkoxycarbonyl,
(5) $C_1$–$C_4$-alkylcarbonyloxy,
(6) $C_3$–$C_8$-cycloalkyl,
(7) phenyl,
(8) substituted phenyl in which the substituents are V and W,
(9) $C_1$–$C_{10}$-alkyl-$S(O)_p$,
(10) $C_3$–$C_8$-cycloalkyl-$S(O)_p$,
(11) phenyl-$S(O)_p$,
(12) substituted phenyl-$S(O)_p$ in which the substituents are V and W,
(13) oxo,
(14) carboxy,
(15) $NR^9R^{10}$,
(16) $C_1$–$C_5$-alkylaminocarbonyl,
(17) di($C_1$–$C_5$-alkyl)aminocarbonyl,
(18) cyano;
(c) perfluoro-$C_1$–$C_4$-alkyl,
(d) $C_2$–$C_{10}$-alkenyl,
(e) $C_2$–$C_{10}$-alkynyl,
(f) $C_3$–$C_8$-cycloalkyl,
(g) substituted $C_3$–$C_8$-cycloalkyl in which one or more substituent(s) is selected from:
(1) Cl, Br, I, F,
(2) hydroxy,
(3) $C_1$–$C_{10}$-alkoxy,
(4) $C_1$–$C_5$-alkoxycarbonyl,
(5) $C_1$–$C_4$-alkylcarbonyloxy,
(6) $C_3$–$C_8$-cycloalkyl,
(7) phenyl,
(8) substituted phenyl in which the substituents are V and W,
(9) $C_1$–$C_{10}$-alkyl-$S(O)_p$ in which p is 0 to 2,
(10) $C_3$–$C_8$-cycloalkyl-$S(O)_p$,
(11) phenyl-$S(O)_p$,
(12) substituted phenyl-$S(O)_p$ in which the substituents are V and W,
(13) oxo,
(14) carboxy,
(15) $NR^9R^{10}$,
(16) $C_1$–$C_5$-alkylaminocarbonyl,
(17) di($C_1$–$C_5$-alkyl)aminocarbonyl,
(18) cyano,
(19) $C_1$–$C_4$-alkylcarbonyl,
(20) ($C_1$–$C_5$) alkyl,
(h) phenyl,
(i) substituted phenyl in which the substituents are V and W,
(j) phenyl-$(CH_2)_r$—$(B)_b$—$(CH_2)_t$—,
(k) substituted aryl-$(CH_2)_r$—$(B)_b$—$(CH_2)_t$— in which the phenyl group is substituted with V and W, (l) 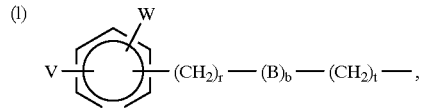

(m) 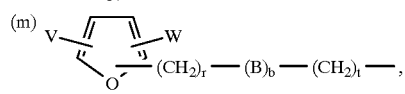

(n) 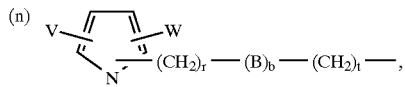

(o) 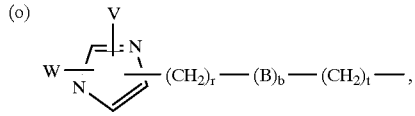

(p) 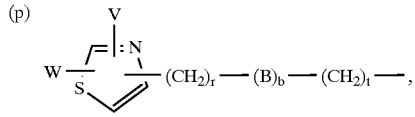

with the proviso that when E is a single bond and n is 0, then $R^7$ is:

(a) substituted $C_1$–$C_{10}$-alkyl in which one or more substituent(s) is selected from:
(1) $C_3$–$C_8$-cycloalkyl,
(2) phenyl,
(3) substituted phenyl in which the substituents are V and W,
(4) $C_3$–$C_8$-cycloalkyl-S(O)$_p$ where p is 0 to 2,
(5) phenyl-S(O)$_p$ where p is 0 to 2,
(6) substituted phenyl-S(O)$_p$ where p is 0 to 2 and the substituents are V and W;
(b) $CF_3$;
(c) $C_3$–$C_8$-cycloalkyl;
(d) substituted $C_3$–$C_8$-cycloalkyl in which the substituent is selected from:
(1) $C_1$–$C_5$-alkyl,
(2) $C_1$–$C_5$-alkoxy;
(e) phenyl;
(f) substituted phenyl as defined above in which the substituents are V and W;
(g) phenyl-$(CH_2)_r$—$(B)_b$—$(CH_2)_t$— in which b is 0 when B is —C(O)—;
(h) substituted phenyl-$(CH_2)_r$—$(B)_b$—$(CH_2)_t$— in which b is 0 when B is —C(O)— and the phenyl group is substituted with V and W;

(i) 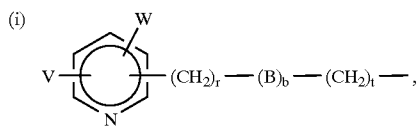

(j) 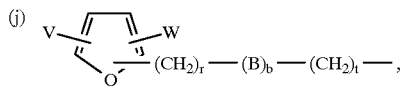

(k) 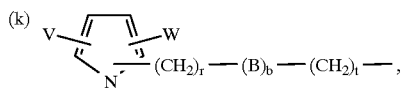

(l) 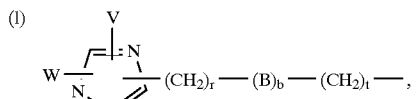

(m) 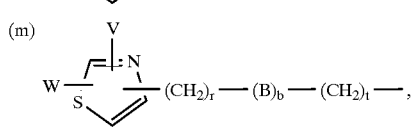

n is 0 or 1;
B is —C(O)—, —S—, or —O—, —$NR^4$—, —$NR^4$C(O)—, or —C(O)$NR^4$;
b is 0 or 1;
r and t are 0 to 2;
u is 1 or 2;
p is 0 to 2;
V and W are each independently selected from:
(a) H,
(b) $C_1$–$C_5$-alkoxy,
(c) $C_1$–$C_5$-alkyl,
(d) hydroxy,
(e) $C_1$–$C_5$-alkyl-S(O)$_p$,
(f) —CN,
(g) —$NO_2$,
(h) —$NR^9R^{10}$,
(i) $C_1$–$C_4$-alkyl-$CONR^9R^{10}$,
(j) —$CO_2R^9$,
(k) $C_1$–$C_5$-alkyl-carbonyl,
(l) trifluoromethyl,
(m) Cl, Br, I, F,
(n) hydroxy-$C_1$–$C_4$-alkyl,
(o) $C_1$–$C_4$-alkyl-$CO_2R^9$,
(p) —1H-tetrazol-5-yl,
(q) —$NHSO_2CF_3$,
(r) aryl,
(s) —$OCONR^9R^{10}$,
(t) —$NR^4CO_2R^9$,
(u) —$NR^4CONR^9R^{10}$,
(v) —$NR^4CON(CH_2CH_2)_2Q$ where Q is O, S(O)$_p$ or $NR^9$,
(w) —$OCON(CH_2CH_2)_2Q$, or
(x) —$CONR^9R^{10}$;

$R^9$ is H, $C_1$–$C_5$-alkyl, phenyl or benzyl;
$R^{10}$ is H, $C_1$–$C_4$-alkyl; or
$R^9$ and $R^{10}$ together may be —$(CH_2)_m$— where m is 3–6;
$R^{11}$ is H, $C_1$–$C_6$-alkyl, $C_2$–$C_4$-alkenyl, $C_1$–$C_4$-alkoxy-$C_1$–$C_4$-alkyl, or —$CH_2$—$C_6H_4R^{20}$;
$R^{12}$ is —CN, —$NO_2$ or —$CO_2R^4$;
$R^{13}$ is H, $C_1$–$C_4$-acyl, $C_1$–$C_6$-alkyl, allyl, $C_3$-$C_6$-cycloalkyl, phenyl or benzyl;
$R^{14}$ is H, $C_1$–$C_8$-alkyl, $C_1$–$C_8$-perfluoroalkyl, $C_3$–$C_6$-cycloalkyl, phenyl or benzyl;
$R^{15}$ is H, $C_1$–$C_6$-alkyl, hydroxy;
$R^{16}$ is H, $C_1$–$C_6$-alkyl, $C_3$–$C_6$-cycloalkyl, phenyl or benzyl;
$R^{17}$ is —$NR^9R^{10}$, —$OR^{10}$, —$NHCONH_2$, —$NHCSNH_2$,

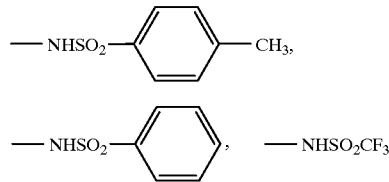

$R^{18}$ and $R^{19}$ are independently $C_1$–$C_4$-alkyl or taken together are —(CH2)$_q$— where q is 2 or 3;
$R^{20}$ is H, —$NO_2$, —$NH_2$, —OH or —$OCH_3$;
$R^{21}$ is $C_1$–$C_5$ alkyl or $CF_3$;
$R^{22}$ is
(a) phenyl, unsubstituted or substituted with 1 or 2 substituents selected from the group consisting of: Cl, Br, I, or F, —O—$C_1$–$C_4$-alkyl, $C_1$–$C_4$- alkyl, —$NO_2$, —$CF_3$, —$SO_2NR^9R^{10}$, —S—$C_1$–$C_4$-alkyl, —OH, —$NH_2$, —$COOR^4$, $C_3$–$C_7$-cycloalkyl, and $C_3$–$C_{10}$-alkenyl;
(b) $C_1$–$C_6$-alkyl, $C_2$–$C_6$-alkenyl or $C_2$–$C_6$-alkynyl each of which is unsubstituted or substituted with one or more substituents selected from the group consisting of aryl, $C_3$–$C_7$-cycloalkyl, Cl, Br, I, F, —OH, —O—$C_1$–$C_4$-alkyl, —$NH_2$, —NH($C_1$–$C_4$-alkyl), —N($C_1$–$C_4$-alkyl)$_2$, —NH—$SO_2R^4$, —$COOR^4$, —$SO_2NHR^9$, and —S—$C_1$–$C_4$-alkyl;
(c) an unsubstituted, monosubstituted or disubstituted aromatic 5 or 6 membered ring comprising one or two heteroatoms selected from the group consisting of N, O, and S, and wherein the substituents are members selected from the group consisting of: —OH, —SH, $C_1$–$C_4$-alkyl, $C_1$–$C_4$- alkyloxy, —$CF_3$, $COOR^4$, Cl, Br, I, F, and $NO_2$; or
(d) $C_3$–$C_7$-cycloalkyl unsubstituted or substituted with one or more substituents selected from the group consisting of: $C_1$–$C_4$-alkyl, —O—$C_1$–$C_4$-alkyl, —S—$C_1$–$C_4$-alkyl, —OH, —COOR$^4$, $C_1$–$C_4$-perfluoroalkyl, Cl, Br, F, and I, or (e) ($C_1$–$C_4$)-perfluoroalkyl;

$R^{23}$ is
(a) aryl,
(b) heteroaryl,
(c) $C_3$–$C_7$-cycloalkyl,
(d) $C_1$–$C_4$-alkyl unsubstituted or substituted with a substituent selected from the group consisting of aryl, heteroaryl, —OH, —SH, $C_1$–$C_4$-alkyl, —O($C_1$–$C_4$-alkyl), —S($C_1$–$C_4$-alkyl), —CF$_3$, Cl, Br, F, I, —NO$_2$, —CO$_2$H, —CO$_2$—$C_1$–$C_4$-alkyl, —NH$_2$, —NH($C_1$–$C_4$-alkyl), —N($C_1$–$C_4$-alkyl)$_2$, —N(CH$_2$CH$_2$)$_2$L where L is a single bond, CH$_2$, O, S(O)$_p$ or NR$^9$, —PO$_3$H, —PO(OH)(O—$C_1$–$C_4$-alkyl);

X is
(a) a carbon-carbon single bond,
(b) —CO—,
(c) —C—,
(d) —S—, (e) —N—,
    |
    R$^{13}$ (f) —CON—,
      |
      R$^{15}$ (g) —NCO—,
     |
     R$^{15}$ (h) —OCH$_2$—,
(i) —CH$_2$O—,
(j) —SCH$_2$—,
(k) —CH$_2$S—,
(l) —NHC(R$^9$)(R$^{10}$)—,
(m) —NR$^9$SO$_2$—,
(n) —SO$_2$NR$^9$—,
(o) —C(R$^9$)(R$^{10}$)NH—,
(p) —CH=CH—,
(q) —CF=CF—,
(r) —CH=CF—,
(s) —CF=CH—,
(t) —CH$_2$CH$_2$—,
(u) —CF$_2$CF$_2$—,
(v) 1,1 and 1,2-disubstituted cyclopropyl, (w)   OR$^{14}$
     |
  —CH—, (x)   OCOR$^{16}$
     |
  —CH—, (y)   NR$^{17}$
     ||
  —C— or (z) R$^{18}$O   OR$^{19}$
      \  /
      —C—  ; and Z is O, NR$^{13}$ or S.

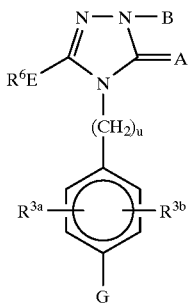

(E)

or a pharmaceutically acceptable salt thereof, wherein:
G is R$^1$ or

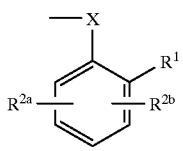

R$^1$ is
(a) —NHSO$_2$R$^{23}$,
(b) —NHSO$_2$NHCOR$^{23}$,
(c) —NHCONHSO$_2$R$^{23}$,
(d) —SO$_2$NHR$^{23}$,
(e) —SO$_2$—NHCOR$^{23}$,
(f) —SO$_2$NHCOR$^{23}$R$^{24}$,
(g) —SO$_2$NHCOOR$^{23}$,
(h) —SO$_2$NHOR$^{23}$,
(i) —CH$_2$SO$_2$NHCOR$^{23}$,
(j) —CH$_2$SO$_2$NHCONHR$^{23}$,
(k) —CO$_2$H, or
(l) —1H-tetrazol-5-yl;

R$^{2a}$ and R$^{2b}$ are each independently:
(a) hydrogen,
(b) —Cl, —Br, —I, or —F,
(c) —CF$_3$,
(d) $C_1$–$C_4$-alkyl, or
(e) $C_1$–$C_4$-alkoxy;

R$^{3a}$ is
(a) —H,
(b) —Cl, —Br, —I, or —F,
(c) $C_1$–$C_6$-alkyl,
(d) $C_1$–$C_6$-alkoxy, or
(e) $C_1$–$C_6$-alkoxy-$C_1$–$C_4$-alkyl;

R$^{3b}$ is
(a) —H,
(b) —Cl, —Br, —I, or —F,
(c) $C_1$–$C_6$-alkyl,
(d) $C_1$–$C_5$-alkylcarbonyloxy,
(e) $C_3$–$C_6$-cycloalkyl,
(f) $C_1$–$C_6$-alkoxy, or
(g) CF$_3$;

R$^4$ is H, $C_1$–$C_6$ alkyl, —CH$_2$-aryl or aryl wherein aryl is phenyl or naphthyl unsubstituted or substituted with one or two substituents selected from the group consisting of: —Cl, —Br, —I, —F, $C_1$–$C_4$-alkyl, $C_1$–$C_4$-alkoxy, NO$_2$, CF$_3$, $C_1$–$C_4$-alkylthio, —OH, —NH$_2$, —CO$_2$H, —CO$_2$—$C_1$–$C_4$-alkyl, —CN and —NHCOR$^9$;

$R^5$ is H or —CH($R^4$)—O—CO—$R^{4a}$, wherein $R^{4a}$ is $C_1$–$C_6$-alkyl, aryl or —$CH_2$-aryl;

E is a single bond, —$NR^{13}(CH_2)_s$—, —$S(O)_x(CH_2)_s$— where x is 0 to 2 and s is 0 to 5, —CH(OH)—, —$O(CH_2)_s$—, —CO—;

$R^6$ is
- (a) phenyl, unsubstituted or substituted with 1 or 2 substituents selected from the group consisting of Cl, Br, I, F, —O—$C_1$–$C_4$-alkyl, $C_1$–$C_4$-alkyl, —$NO_2$, —$CF_3$, —$SO_2NR^9R^{10}$, —S—$C_1$–$C_4$-alkyl, —OH, —$NH_2$, $C_3$–$C_7$-cycloalkyl, and $C_3$–$C_{10}$-alkenyl;
- (b) $C_1$–$C_6$-alkyl, $C_2$–$C_6$-alkenyl or $C_2$–$C_6$-alkynyl each of which is unsubstituted or substituted with one or more substituents selected from the group consisting of: aryl, $C_3$–$C_7$-cycloalkyl, Cl, Br, I, F, —OH, —O—$C_1$–$C_4$-alkyl, —$NH_2$, —NH($C_1$–$C_4$-alkyl), —N($C_1$–$C_4$-alkyl)$_2$, —NH—$SO_2R^4$, —$COOR^4$, —$SO_2NHR^9$, and —S—$C_1$–$C_4$-alkyl;
- (c) an unsubstituted, monosubstituted or disubstituted aromatic 5- or 6-membered ring which can contain one or two heteroatoms selected from the group consisting of N, O, and S, and wherein the substituents are members selected from the group consisting of —OH, —SH, $C_1$–$C_4$-alkyl, $C_1$–$C_4$-alkyloxy, —$CF_3$, Cl, Br, I, F, or $NO_2$;
- (d) mono-, di-, tri- or polyfluoro-$C_1$–$C_5$-alkyl;
- (e) $C_3$–$C_7$-cycloalkyl, unsubstituted or substituted with one or more substituents selected from the group consisting of $C_1$–$C_4$-alkyl, O—$C_1$–$C_4$-alkyl, S—$C_1$–$C_4$-alkyl, OH, perfluoro-$C_1$–$C_4$-alkyl, Cl, Br, F, and I; or
- (f) $C_3$–$C_7$-cycloalkyl-$C_1$–$C_3$-alkyl, wherein the cycloalkyl is unsubstituted or substituted as in (e) above;

A is =O, =S or =$NR^{21}$;

B is
- (a) H provided A is not $NR^{21}$,
- (b) $C_1$–$C_{10}$-alkyl,
- (c) substituted $C_1$–$C_{10}$-alkyl in which one or more substituent(s) is selected from the group consisting of:
  - (1) I, Br, Cl, or F,
  - (2) hydroxy,
  - (3) $C_1$–$C_{10}$-alkoxy,
  - (4) $C_1$–$C_5$-alkoxycarbonyl,
  - (5) $C_1$–$C_4$-alkylcarbonyloxy,
  - (6) $C_3$–$C_8$-cycloalkyl,
  - (7) phenyl, naphthyl or biphenyl,
  - (8) substituted phenyl, naphthyl or biphenyl in which the substituents are $V_1$, $V_2$, $V_3$, $V_4$ and $V_5$,
  - (9) $C_1$–$C_{10}$-alkyl-S(O)$_p$ in which p is 0 to 2,
  - (10) $C_3$–$C_8$-cycloalkyl-S(O)$_p$,
  - (11) phenyl-S(O)$_p$,
  - (12) substituted phenyl-S(O)$_p$ in which the substituents are $V_1$–$V_5$,
  - (13) oxo,
  - (14) carboxy,
  - (15) $NR^9R^9$,
  - (16) $C_1$–$C_5$-alkylaminocarbonyl,
  - (17) di($C_1$–$C_5$-alkyl)aminocarbonyl,
  - (18) cyano,
  - (19) —$OCONR^{21}R^{22}$,
  - (20) —$NR^{21}COR^{22}$,
  - (21) —$NR^{21}CO_2R^{22}$,
  - (22) —$NR^{21}CONR^{21}R^{22}$,
  - (23) —$NR^{21}CON(CH_2CH_2)_2L$, or
  - (24) —$OCON(CH_2CH_2)L$, wherein L is a single bond, $CH_2$, O, S(O)$_p$ or $NR^9$,
- (d) $C_2$–$C_{10}$-alkenyl,
- (e) $C_2$–$C_{10}$-alkynyl,
- (f) $C_3$–$C_8$-cycloalkyl,
- (g) substituted $C_3$–$C_8$-cycloalkyl or substituted $C_3$–$C_8$-cycloalkyl-$C_1$–$C_4$-alkyl having one or more substituents selected from the group consisting of:
  - (1) Cl, Br, F, or I,
  - (2) hydroxy,
  - (3) $C_1$–$C_6$-alkyl,
  - (4) $C_1$–$C_6$-alkoxy,
  - (5) $C_1$–$C_4$-alkylcarbonyloxy,
  - (6) $C_1$–$C_5$-alkoxycarbonyl,
  - (7) carboxy,
  - (8) oxo,
  - (9) $C_1$–$C_5$-alkylaminocarbonyl,
  - (10) di($C_1$–$C_5$-alkyl)aminocarbonyl,
  - (11) $C_1$–$C_4$-alkylcarbonyl,
  - (12) phenyl, naphthyl or biphenyl,
  - (13) substituted phenyl, naphthyl or biphenyl in which the substituents are $V_1$, $V_2$, $V_3$, $V_4$ and $V_5$,
  - (14) —$NR^{21}COR^{22}$,
  - (15) —$NR^{21}CO_2R^{22}$,
  - (16) —$OCONR^{21}R^{22}$, and
  - (17) —CN,
- (h) phenyl, naphthyl or biphenyl,
- (i) substituted phenyl, naphthyl or biphenyl in which the substituents are $V_1$, $V_2$, $V_3$, $V_4$ and $V_5$,
- (j) phenyl—$(CH_2)_r$—(Q)$_c$—$(CH_2)_t$—,
- (k) substituted phenyl-$(CH_2)_r$—(Q)$_c$—$(CH_2)_t$— in which the phenyl group is substituted with $V_1$, $V_2$, $V_3$, $V_4$ and $V_5$, (l) 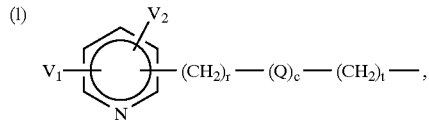

(m) 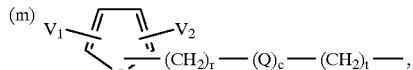

(n) 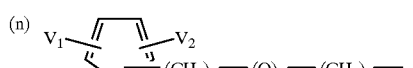

(o) 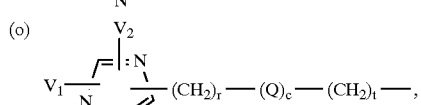

(p) 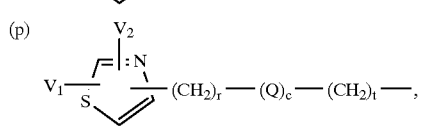

$R^9$ is H, $C_1$–$C_5$-alkyl, aryl or —$CH_2$-aryl;

$R^{10}$ is H, $C_1$–$C_4$-alkyl, or $R^9$ and $R^{10}$ together can be —$(CH_2)_m$—, where m is 3–6;

$R^{11}$ is H, $C_1$–$C_6$-alkyl, $C_2$–$C_4$-alkenyl, $C_1$–$C_4$-alkoxy-$C_1$–$C_4$-alkyl, or —$CH_2$—$C_6H_4R^{20}$;

$R^{12}$ is —CN, —$NO_2$ or —$CO_2R^4$;

$R^{13}$ is H, $C_2$–$C_4$-alkanoyl, $C_1$–$C_6$-alkyl, allyl, $C_3$–$C_6$-cycloalkyl, phenyl or benzyl;

$R^{14}$ is H, $C_1$–$C_8$-alkyl, $C_1$–$C_8$-perfluoroalkyl, $C_3$–$C_6$-cycloalkyl, phenyl or benzyl;

$R^{15}$ is H, $C_1$–$C_6$-alkyl, hydroxy;

$R^{16}$ is H, $C_1$–$C_6$-alkyl, $C_3$–$C_6$-cycloalkyl, phenyl or benzyl;

$R^{17}$ is $-NR^9R^{10}$, $-OR^{10}$, $-NHCONH_2$, $-NHCSNH_2$, $-NHSO_2CF_3$,

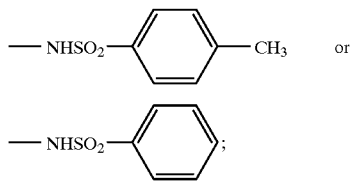

$R^{18}$ and $R^{19}$ are independently $C_1$-$C_4$-alkyl or taken together are $-(CH_2)_q-$ where q is 2 or 3;

$R^{20}$ is H, $-NO_2$, $-NH_2$, $-OH$ or $-OCH_3$;

$R^{21}$ is
(a) H;
(b) phenyl, unsubstituted or substituted with 1 or 2 substituents selected from the group consisting of: Cl, Br, I, F, $-O-C_1$-$C_4$-alkyl, $C_1$-$C_4$-alkyl, $-NO2$, $-CF_3$, $-SO_2NR^9R^{10}$, $-S-C_1$-$C_4$-alkyl, $-OH$, $-NH_2$, $-COOR^4$, $C_3$-$C_7$-cycloalkyl and $C_3$-$C_{10}$-alkenyl;
(c) $C_1$-$C_6$-alkyl, $C_2$-$C_6$-alkenyl or $C_2$-$C_6$-alkynyl each of which is unsubstituted or substituted with one or more substituents selected from the group consisting of aryl, $C_3$-$C_7$-cyclo-alkyl, Cl, Br, I, F, $-OH$, $-O-C_1$-$C_4$-alkyl, $-NH_2$, $-NH(C_1$-$C_4$-alkyl), $-N(C_1$-$C_4$-alkyl)$_2$, $-NH-SO_2R^4$, $-COOR^4$, $-SO_2NHR^9$, and $-S-C_1$-$C_4$-alkyl;
(d) an unsubstituted, monosubstituted or disubstituted aromatic 5 or 6 membered ring comprising one or two heteroatoms selected from the group consisting of N, O, and S, and wherein the substituents are members selected from the group consisting of $-OH$, $-SH$, $C_1$-$C_4$-alkyl, $C_1$-$C_4$-alkyloxy, $-CF_3$, $-COOR^4$, Cl, Br, I, F, and $NO_2$; or
(e) $C_3$-$C_7$-cycloalkyl, unsubstituted or substituted with one or more substituents selected from the group consisting of: $C_1$-$C_4$-alkyl, $-O-C_1$-$C_4$-alkyl, $-S-C_1$-$C_4$-alkyl, $-OH$, $-COOR^4$, $C_1$-$C_4$-perfluoroalkyl, Cl, Br, F, and I; or
(f) $(C_1$-$C_4)$-perfluoroalkyl;

$R^{22}$ is $R^{21}$ excluding H;

$R^{23}$ is
(a) aryl;
(b) heteroaryl, is an unsubstituted, monosubstituted or disubstituted 5- or 6- membered aromatic ring, such as thiazole, imidazole, pyrazole, oxazole, pyridine, thiazone, pyrazine, pyrimidine or the like, which contains from 1 to 3 heteroatoms selected from the group consisting of O, N and S and wherein the substituents are members selected from the group consisting of $-OH$, $-SH$, $C_1$-$C_4$-alkyl, $C_1$-$C_4$-alkoxy, $-CF_3$, Cl, Br, F, I, $-NO_2$, $-CO_2H$, $-CO_2$-$C_1$-$C_4$-alkyl, $-NH_2$, $-NH(C_1$-$C_4$-alkyl) and $-N(C_1$-$C_4$-alkyl)$_2$;
(c) $C_3$-$C_7$-cycloalkyl optionally substituted with one or more substituents selected from the group consisting of: $C_1$-$C_4$-alkyl, $-O-C_1$-$C_4$-alkyl, $-S-C_1$-$C_4$-alkyl, $-OH$, $-COOR^4$, perfluoro-$C_1$-$C_4$-alkyl, Cl, Br, F, and I;
(d) $C_1$-$C_8$-alkyl unsubstituted or substituted with one or two substituents selected from the group consisting of: aryl, heteroaryl, $-OH$, $-SH$, $C_1$-$C_4$-alkyl, $C_2$-$C_4$-alkenyl, $C_2$-$C_4$-alkynyl, $-O(C_1$-$C_4$-alkyl), $S(C_1$-$C_4$-alkyl), $C_3$-$C_8$-cycloalkyl, $-CF_3$, Cl, Br, F, I, $-NO_2$, $-CO_2H$, $-CO_2$-$C_1$-$C_4$-alkyl, $-PO_3H$, $-PO(OH)(O-C_1$-$C_4$-alkyl), $-PO(OR^4)(R^9)$, $-NH_2$, $-NH(C_1$-$C_4$-alkyl), $-N(C_1$-$C_4$-alkyl)$_2$, $-NH$-aryl, $-N(aryl)_2$, $-N(CH_2CH_2)_2L$, $-NR^4COR^{22}$, $-CONR^4R^{22}$, $-OCONR^4R^{22}$, $SO_2NR^4R^{22}$, $-NR^4SO_2R^{22}$;
(e) polyfluoro-$C_1$-$C_4$-alkyl;
(f) $-NR^{21}R^{21}$; or
(g) $-N(CH_2CH_2)L$;

X is
(a) a single bond,
(b) $-CO-$,
(c) $-O-$,
(d) $-S-$,
(e) 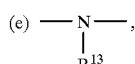
(f) 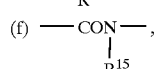
(g) 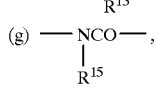

(h) $-OCH_2-$,
(i) $-CH_2O-$,
(j) $-SCH_2-$,
(k) $-CH_2S-$,
(l) $-NHC(R^9)(R^{10})-$,
(m) $-NR^9SO_2-$,
(n) $-SO_2NR^9-$,
(o) $-C(R^9)(R^{10})NH-$,
(p) $-CH=CH-$,
(q) $-CF=CF-$,
(r) $-CH=CF-$,
(s) $-CF=CH-$,
(t) $-CH_2CH_2-$,
(u) $-CF_2CF_2-$,
(v) 1,1-dimethylcyclopropyl or 1,2-dimethylcyclopropyl, (w) 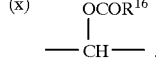

(x) 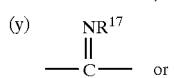

(y) 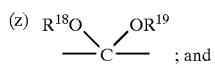 or (z) 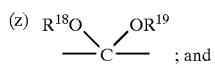 ; and

Q is $-C(O)-$, $-S-$, $-O-$ or $-NR^4$;

c is 0 or 1;

r and t are 0 to 2;

$V_1$, $V_2$, $V_3$, $V_4$ and $V_5$ are each independently selected from:
(a) H,
(b) $C_1$-$C_5$-alkoxy,
(c) $C_1$-$C_5$-alkyl,
(d) hydroxy,
(e) $C_1$-$C_5$-alkyl-$S(O)_p$,
(f) $-CN$,
(g) $-NO_2$, (h) —NR⁹R¹⁰,
(i) $C_1$–$C_5$-alkyl—CONR⁹R¹⁰,
(j) —CONR⁹R¹⁰,
(k) —CO₂R⁹,
(l) $C_1$–$C_5$-alkyl-carbonyl,
(m) CF₃,
(n) I, Br, Cl, F,
(o) hydroxy-$C_1$–$C_4$-alkyl-,
(p) carboxy-$C_1$–$C_4$-alkyl-,
(q) —1H-tetrazol-5-yl,
(r) —NH—SO₂CF₃,
(s) aryl,
(t) $C_1$–$C_5$-alkyl-CO₂R⁹,
(u) aryloxy,
(v) aryl-$C_1$–$C_3$-alkoxy,
(w) aryl-$C_1$–$C_3$-alkyl,
(x) carboxyphenyl,
(y) heteroaryl,
(z) 2-oxazolin-2-yl optionally bearing one or more $C_1$–$C_4$-alkyl substituents,
(aa) —(CH₂)$_t$OCOR²²,
(bb) —(CH₂)$_t$OCONR²¹R²²,
(cc) —(CH₂)$_t$NR²¹COR²²,
(dd) —(CH₂)$_t$NR²¹CO₂R²²,
(ee) —(CH₂)$_t$NR²¹CONR²³R²²,
(ff) —(CH₂)$_t$NR²¹CON(CH₂CH₂)₂L,
(gg) —(CH₂)$_t$OCON(CH₂CH₂)₂L,
(hh) —N(CH₂CH₂)₂L,
(ii) —$C_1$–$C_5$-alkyl-CON(CH2CH₂)₂L, or
(jj) —CON(CH₂CH₂)L;
u is 1 or 2;
Z is O, NR¹³ or S.

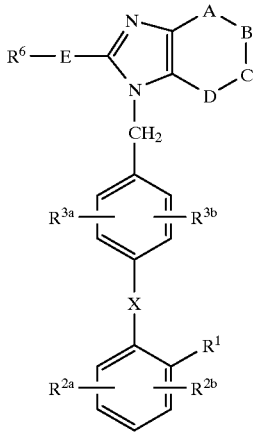

(F)

or a pharmaceutically acceptable salt thereof, wherein:
R¹ is
(a) —NHSO₂R²³,
(b) —NHSO₂NHCOR²³,
(c) —NHCONHSO₂R²³,
(d) —SO₂NHR²³,
(e) —SO₂NHCOR²³,
(f) —SO₂NHCONR⁹R²³,
(g) —SO₂NHCOOR²³,
(h) —SO₂NHOR²³,
(i) —CH₂SO₂NHCOR²³,
(j) —CH₂SO₂NHCONHR²³,
(k) —CO₂H, or
(l) —1H-tetrazol-5-yl;
R²ᵃ and R²ᵇ are independently H, Cl, Br, I, F, —NO₂, —NH₂, $C_1$–$C_4$-alkylamino, di($C_1$–$C_4$-alkyl)amino, —SO₂—NHR⁹, CF₃, $C_1$–$C_4$-alkyl, or $C_1$–$C_4$-alkoxy;

R³ᵃ is
(a) H,
(b) Cl, Br, I, F,
(c) $C_1$–$C_6$-alkyl,
(d) $C_1$–$C_6$-alkoxy,
(e) $C_1$–$C_6$-alkoxyalkyl;
R³ᵇ is
(a) H,
(b) Cl, Br, I, F,
(c) NO₂,
(d) $C_1$–$C_6$-alkyl,
(e) $C_1$–$C_6$-acyloxy,
(f) $C_1$–$C_6$-cycloalkyl,
(g) $C_1$–$C_6$-alkoxy,
(h) —NHSO₂R⁴,
(i) hydroxy $C_1$–$C_4$-alkyl,
(j) aryl $C_1$–$C_4$-alkyl,
(k) $C_1$–$C_4$-alkylthio,
(l) $C_1$–$C_4$-alkyl-sulfinyl,
(m) $C_1$–$C_4$-alkyl-sulfonyl,
(n) NH₂,
(o) $C_1$–$C_4$-alkylamino,
(p) $C_1$–$C_4$-dialkylamino,
(q) fluoro $C_1$–$C_4$-alkyl,
(r) —SO₂—NHR⁹,
(s) aryl, or wherein aryl is phenyl or naphthyl optionally substituted with one or two substituents selected from the group consisting of Cl, Br, I, F, $C_1$–$C_4$-alkyl, $C_1$–$C_4$-alkoxy, NO₂, CF₃, $C_1$–$C_4$-alkylthio, OH, NH₂, NH($C_1$–$C_4$-alkyl), N($C_1$–$C_4$-alkyl)₂, CO₂H, and CO₂—$C_1$–$C_4$-alkyl,
(t) furyl;
R⁴ is H, $C_1$–$C_6$ alkyl, aryl or —CH₂-aryl;
R⁴ᵃ is $C_1$–$C_6$-alkyl, aryl or —CH₂-aryl;
R⁵ is H,

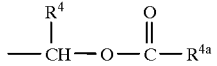

E is a single bond, —NR¹³(CH₂)$_s$—, —S(O)$_x$—(CH₂)$_s$— where x is 0 to 2 and s is 0 to 5, —CH(OH)—, —O—, —CO—;
R⁶ is
(a) aryl unsubstituted or substituted with 1 or 2 substituents selected from the group consisting of Cl, Br, I, F, —O—$C_1$–$C_4$-alkyl, $C_1$–$C_4$-alkyl, —NO₂, —CF₃, —SO₂NR⁹R¹⁰, —S—$C_1$–$C_4$-alkyl, —OH, —NH₂, $C_3$–$C_7$-cycloalkyl, $C_3$–$C_{10}$-alkenyl;
(b) $C_1$–$C_9$-alkyl, $C_2$–$C_6$-alkenyl or $C_2$–$C_6$-alkynyl each of which can be unsubstituted or substituted with a substituent selected from the group consisting of aryl, $C_3$–$C_7$-cycloalkyl, Cl, Br, I, F, —OH, —NH₂, —NH($C_1$–$C_4$-alkyl), —CF₂CF₃, —N($C_1$–$C_4$-alkyl)₂, —NH—SO₂R⁴, —COOR⁴, —CF₃, —CF₂CH₃, —SO₂NHR⁹; or
(c) an unsubstituted, monosubstituted or disubstituted aromatic 5 or 6 membered cyclic ring which can contain one or two members selected from the group consisting of N, O, S, and wherein the substituents are members selected from the group consisting of —OH, —SH, $C_1$–$C_4$-alkyl, $C_1$–$C_4$-alkyloxy, —CF₃, Cl, Br, I, F, or NO₂;
(d) perfluoro-$C_1$–$C_4$-alkyl;
(e) $C_3$–$C_7$-cycloalkyl optionally mono- or disubstituted with $C_1$–$C_4$-alkyl or —CF₃;

$R^9$ is H, $C_1$–$C_5$-alkyl, aryl or —$CH_2$-aryl;

$R^{10}$ is H, $C_1$–$C_4$-alkyl;

$R^{11}$ is H, $C_1$–$C_6$-alkyl, $C_2$–$C_4$-alkenyl, $C_1$–$C_4$-alkoxy-$C_1$–$C_4$-alkyl, or

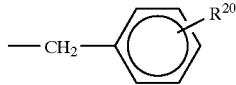

$R^{12}$ is —CN, —$NO_2$ or —$CO_2R^4$;

$R^{13}$ is H, —CO($C_1$–$C_4$-alkyl), $C_1$–$C_6$-alkyl, allyl, $C_3$–$C_6$-cycloalkyl, phenyl or benzyl;

$R^{14}$ is H, $C_1$–$C_8$-alkyl, $C_1$–$C_8$-perfluoroalkyl, $C_3$–$C_6$-cycloalkyl, phenyl or benzyl;

$R^{15}$ is H, $C_1$–$C_6$-alkyl;

$R^{16}$ is H, $C_1$–$C_6$-alkyl, $C_3$–$C_6$-cycloalkyl, phenyl or benzyl;

$R^{17}$ is —$NR^9R^{10}$, —$OR^{10}$, —$NHCONH_2$, —$NHCSNH_2$,

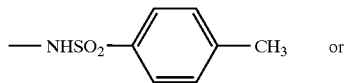   or

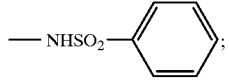;

$R^{18}$ and $R^{19}$ are independently $C_1$–$C_4$-alkyl or taken together are —$(CH_2)_q$— where q is 2 or 3;

$R^{20}$ is H, —$NO_2$, —$NH_2$, —OH or —$OCH_3$;

$R^{22}$ is
 (a) phenyl, unsubstituted or substituted with 1 or 2 substituents selected from the group consisting of: Cl, Br, I, or F, —O—$C_1$–$C_4$-alkyl, $C_1$–$C_4$-alkyl, —$NO_2$, —$CF_3$, —$SO_2NR^9R^{10}$, —S—$C_1$–$C_4$-alkyl, —OH, —$NH_2$, —$COOR^4$, $C_3$–$C_7$-cycloalkyl, and $C_3$–$C_{10}$-alkenyl;
 (b) $C_1$–$C_6$-alkyl, $C_2$–$C_6$-alkenyl or $C_2$–$C_6$-alkynyl each of which is unsubstituted or substituted with one or more substituents selected from the group consisting of aryl, $C_3$–$C_7$-cycloalkyl, Cl, Br, I, F, —OH, —O—$C_1$–$C_4$-alkyl, —$NH_2$, —$NH(C_1$–$C_4$-alkyl), —$N(C_1$–$C_4$-alkyl)$_2$, —NH—$SO_2R^4$, —$COOR^4$, —$SO_2NHR^9$, and —S—$C_1$–$C_4$-alkyl;
 (c) an unsubstituted, monosubstituted or disubstituted aromatic 5 or 6 membered ring comprising one or two heteroatoms selected from the group consisting of N, O, and S, and wherein the substituents are members selected from the group consisting of: —OH, —SH, $C_1$–$C_4$-alkyl, $C_1$–$C_4$-alkyloxy, —$CF_3$, —$COOR^4$, Cl, Br, I, F, and $NO_2$; or
 (d) $C_3$–$C_7$-cycloalkyl unsubstituted or substituted with one or more substituents selected from the group consisting of: $C_1$–$C_4$-alkyl, —O—$C_1$–$C_4$-alkyl, —S—$C_1$–$C_4$-alkyl, —OH, —$COOR^4$, $C_1$–$C_4$-perfluoroalkyl, Cl, Br, F, and I; or
 (e) ($C_1$–$C_4$)-perfluoroalkyl;

$R^{23}$ is
 (a) aryl,
 (b) heteroaryl,
 (c) $C_3$–$C_4$-cycloalkyl,
 (d) $C_1$–$C_8$-alkyl which can be unsubstituted or substituted with one or two substituents selected from the group consisting of: aryl, heteroaryl, wherein heteroaryl is an unsubstituted, monosubstituted or disubstituted five- or six-membered aromatic ring which can optionally contain 1 to 3 heteroatoms selected from the group consisting of O, N or S and wherein the substituents are members selected from the group consisting of: —OH, —SH, —$C_1$–$C_4$-alkyl, —O($C_1$–$C_4$-alkyl), —S($C_1$–$C_4$-alkyl), —$C_3$–$C_8$-cycloalkyl, —$CF_3$, Cl, Br, F, I, —$NO_2$, —$CO_2H$, —$CO_2$—$C_1$–$C_4$-alkyl, —$CONR^4R^{22}$, —$OCONR^4R^{22}$, —$NH_2$, —$NH(C_1$–$C_4$-alkyl), —$NHCOR^{4a}$, $NR^4COOR^9$, —$N(C_1$–$C_4$-alkyl)$_2$, —$NR^4COR^{22}$, —$NR^4SO_2R^{22}$, —$SO_2NR^4R^{22}$, —$PO_3H$, —PO—(OH)($C_1$–$C_4$-alkyl), —PO(OH)(aryl), or —PO(OH)(O—$C_1$–$C_4$-alkyl), or
 (e) perfluoro-$C_1$–$C_4$-alkyl;

X is absent or is
 (a) a carbon-carbon single bond,
 (b) —CO—,
 (c) —O—,
 (d) —S—,

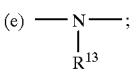

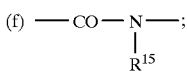

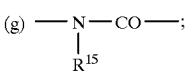

(h) —$OCH_2$—,
 (i) —$CH_2O$—,
 (j) —$SCH_2$—,
 (k) —$CH_2S$—,
 (l) —$NHC(R^9)(R^{10})$,
 (m) —$NR^9SO_2$—,
 (n) —$SO_2NR^9$—,
 (o) —$C(R^9)(R^{10})NH$—,
 (p) —CH=CH—,
 (q) —CF=CF—,
 (r) —CH=CF—,
 (s) —CF=CH—,
 (t) —$CH_2CH_2$—,
 (u) —$CF_2CF_2$—, (u) —$CF_2CF_2$—,

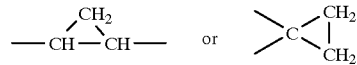

(w) 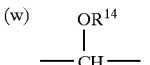

(x) 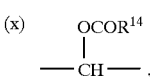

(y) 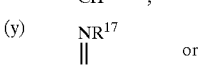   or (z) 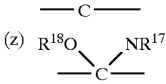

Z is O, $NR^{13}$ or S;

—A—B—C—D— represents the constituent atoms of a 6-member carbocycle or a 6-member saturated or unsaturated heterocyclic ring with the imidazole to which they are attached containing 1 to 3 nitrogen atoms and includes the following:

(a) $-\underset{R^7}{C}=\underset{R^7}{C}-\underset{R^7}{C}=\underset{R^7}{C}-$, (b) $-\underset{R^7}{C}=\underset{R^7}{C}-\underset{R^7}{C}=N-$, (c) $-N=\underset{R^7}{C}-\underset{R^7}{C}=\underset{R^7}{C}-$, (d) $-\underset{R^7}{C}=\underset{R^7}{C}-N=\underset{R^7}{C}-$, (e) $-\underset{R^7}{C}=N-\underset{R^7}{C}=\underset{R^7}{C}-$, (f) $-\underset{R^7}{C}=\underset{R^7}{C}-N=N-$, (g) $-N=N-\underset{R^7}{C}=\underset{R^7}{C}-$, (h) $-\underset{R^7}{C}=N-N=\underset{R^7}{C}-$, (i) $-N=\underset{R^7}{C}-\underset{R^7}{C}=N-$, (j) $-N=\underset{R^7}{C}-N=\underset{R^7}{C}-$, (k) $-\underset{R^7}{C}=N-\underset{R^7}{C}=N-$, (l) $-N=N-N=\underset{R^7}{C}-$, (m) $-\underset{R^7}{C}=N-N=N-$, (n) $-N=N-\underset{R^7}{C}=N-$, (o) $-N=\underset{R^7}{C}-N=N-$, (p) $-\underset{\parallel}{C}-\underset{R^8}{N}-\underset{\parallel}{C}-\underset{R^8}{N}-$, (q) $-\underset{R^8}{N}-\underset{\parallel}{C}-\underset{R^8}{N}-\underset{\parallel}{C}-$, (r) $-\underset{R^7}{C}=\underset{R^7}{C}-\underset{\parallel}{C}-\underset{R^8}{N}-$, (s) $-\underset{R^8}{N}-\underset{\parallel}{C}-\underset{R^7}{C}=N-$, (t) $-N=\underset{R^7}{C}-\underset{\parallel}{C}-\underset{R^8}{N}-$, (u) $-\underset{R^7}{C}=\underset{R^7}{C}-\underset{\parallel}{C}-\underset{R^8}{N}-$, (v) $-\underset{R^7}{C}=\underset{R^7}{C}-\underset{R^8}{N}-\underset{\parallel}{C}-$, (w) $-\underset{R^8}{N}-\underset{\parallel}{C}-\underset{R^7}{C}=\underset{R^7}{C}-$, (x) $-\underset{\parallel}{C}-\underset{R^8}{N}-\underset{R^7}{C}=\underset{R^7}{C}-$, (y) $-\underset{R^8}{N}-\underset{\parallel}{C}-N=N-$, (y) $-\underset{R^8}{N}-\underset{\parallel}{C}-N=N-$, (z) $-N=N-\underset{\parallel}{C}-\underset{R^8}{N}-$, (aa) $-\underset{\parallel}{C}-\underset{R^8}{N}-N=N-$, (ab) $-\underset{\parallel}{C}-\underset{R^8}{N}-\underset{R^7}{C}=N-$, (ac) $-N=\underset{R^7}{C}-\underset{R^8}{N}-\underset{\parallel}{C}-$, (ad) $-\underset{\parallel}{C}-\underset{R^8}{N}-\underset{R^8}{N}-\underset{\parallel}{C}-$, (ae) 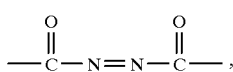

(af) 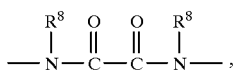

(ag) 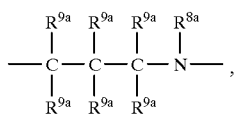

(ah) 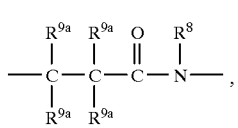

(ai) 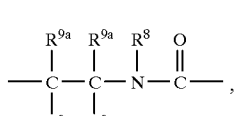

(aj) 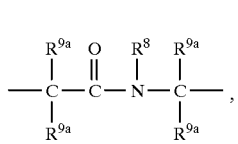

(ak) 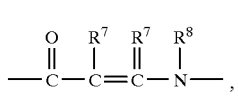

(al) 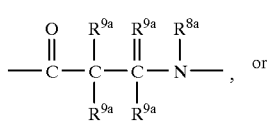 or (am) 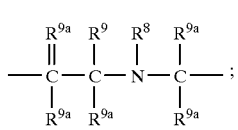

$R^7$ groups can be the same or different and represent:
a) hydrogen,
b) $C_1$–$C_6$ straight or branched chain alkyl, or $C_2$–$C_6$ alkenyl, or alkynyl each of which is unsubstituted or substituted with:
 i) —OH,
 ii) $C_1$–$C_4$-alkoxy,
 iii) —$CO_2R^4$,
 iv) —$OCOR^4$,
 v)

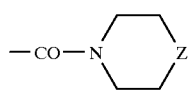

vi) —$CON(R^4)_2$, vii) 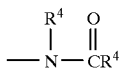

viii) —$N(R^4)_2$,
ix) aryl as defined above,
x) heterocyclic as defined in (p) below,
xi) —$S(O)_xR^{23}$,
xii) tetrazol-5-yl,
xiii) —$CONHSO_2R^{23}$,
xiv) —$SO_2NH$-heteroaryl,
xv) —$SO_2NHCOR^{23}$, xvi) 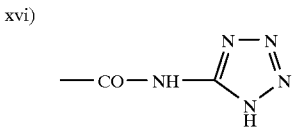

xvii) 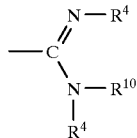

xviii) 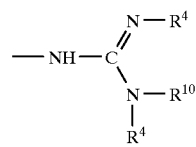

xix) —$PO(OR^4)_2$,
xx) —$PO(OR^4)R^9$,
c) Cl, Br, I, F,
d) perfluoro-$C_1$–$C_4$-alkyl,
e) —OH,
f) —$NH_2$, (g) 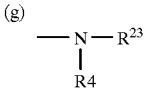

(h) 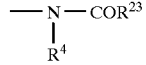

i) —$OR^{23}$,
j) —$CO_2R^4$,
k) —$CON(R^4)_2$,
l) —NH—$C_3$–$C_7$-cycloalkyl,
m) $C_3$–$C_7$-cycloalkyl,
n) aryl as defined above, or
o) heterocyclic which is a five- or six-membered saturated or unsaturated ring containing up to three heteroatoms selected from the group consisting of O, N or S wherein S may be in the form of sulfoxide or sulfone and which may be optionally substituted with one or two substituents which are members selected from the group consisting of halo (Cl, Br, F, I), $C_1$–$C_4$-alkyl, $C_1$–$C_4$-alkoxy, $C_1$–$C_4$-$S(O)_x$— where x is as defined above, $CF_3$, $NO_2$, OH, $CO_2H$, $CO_2$—$C_1$–$C_4$-alkyl, or —$N(R^4)_2$, p) —CN,
q) (CH2)$_n$N— wherein n is 4 to 6,
r) —SO$_2$N(R$^4$)$_2$,
s) tetrazol-5-yl,
t) —CONHSO$_2$R$^{23}$,
u) —PO(OR$^4$)$_2$,
v) —NHSO$_2$CF$_3$,
w) —SO$_2$NH-heteroaryl,
x) —SO$_2$NHCOR$^{23}$,
y) —S(O)$_x$—R$^{23}$,

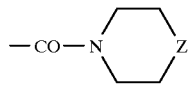

z)
aa) —PO(OR$^4$)R$^9$,
bb) —NHSO$_2$R$^{23}$,
cc) —NHSO$_2$NHR$^{23}$,
dd) —NHSO$_2$NHCOR$^{23}$,
ee) —NHCONHSO$_2$R$^{23}$,
ff) —N(R$^4$)CO$_2$R$^{23}$,
gg)

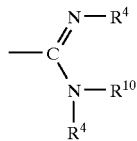

hh) —CO—aryl,
ii)

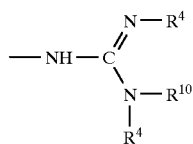

jj) —CO—C$_1$–C$_4$-alkyl,
kk) —SO$_2$NH—CN, ll)

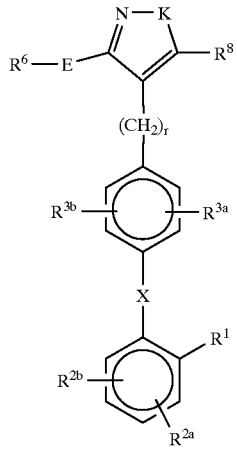

mm)

R$^8$ groups can be the same or different and represent:
 a) hydrogen,
 b) C$_1$–C$_6$-alkyl or alkenyl either unsubstituted or substituted with hydroxy, C$_1$–C$_4$-alkoxy, —N(R$^4$)$_2$, —CO$_2$R$^4$, or C$_3$–C$_5$-cycloalkyl,
 c) C$_3$–C$_5$-cycloalkyl;
R$^{8a}$ is R$^8$ or C$_1$–C$_4$-acyl;
R$^{9a}$ groups can be the same or different and represent:
 a) hydrogen,
 b) C$_1$–C$_6$-alkyl either unsubstituted or substituted with i) hydroxy,
 ii) —CO$_2$R$^4$,
 iii) —CONHR$^4$, or
 iv) —CON(R$^4$)$_2$.

(G)

or a pharmaceutically acceptable salt thereof, herein:
K is O, S, or NR$^7$;
 R$^1$ is:
  (a) —NHSO$_2$R$^{23}$,
  (b) —NHSO$_2$NHCOR$^{23}$,
  (c) —NHCONHSO$_2$R$^{23}$,
  (d) —SO$_2$NHR$^{23}$,
  (e) —SO$_2$NHCOR$^{23}$,
  (f) —SO$_2$NHCONR$^9$R$^{23}$,
  (g) —SO$_2$NHCOOR$^{23}$,
  (h) —SO$_2$NHOR$^{23}$,
  (i) —CH$_2$SO$_2$NHCOR$^{23}$,
  (j) —CH$_2$SO$_2$NHCONHR$^{23}$,
  (k) —CO$_2$H, or
  (l) —1H-tetrazol-5-yl;
 R$^{2a}$ and R$^{2b}$ are independently
  (a) H,
  (b) Cl, Br, I, F,
  (c) CF$_3$,
  (d) C$_1$–C$_4$-alkyl, or
  (e) C$_1$–C$_4$-alkoxy;
 R$^{3a}$ is
  (a) H,
  (b) Cl, Br, I, F,
  (c) C$_1$–C$_6$-alkyl,
  (d) C$_1$–C$_6$-alkoxy, or
  (e) C$_1$–C$_6$-alkoxy-C$_1$–C$_4$-alkyl;
 R$^{3b}$ is
  (a) H,
  (b) Cl, Br, I, F,
  (c) C$_1$–C$_6$-alkyl,
  (d) C$_2$–C$_6$-alkanoyloxy,
  (e) C$_3$–C$_6$-cycloalkyl,
  (f) C$_1$–C$_6$-alkoxy, or
  (g) CF$_3$;
 R$^4$ is H, C$_1$–C$_6$ alkyl, —CH$_2$-aryl, or aryl, wherein aryl is phenyl or naphthyl either unsubstituted or substituted with one, two or three substituents selected from the group consisting of Cl, Br, I, F, C$_1$–C$_4$-alkyl, C$_1$–C$_4$-alkoxy, NO$_2$, CF$_3$, C$_1$–C$_4$-alkylthio, OH, NH$_2$, —NH(C$_1$–C$_4$-alkyl), —N(C$_1$–C$_4$-alkyl)$_2$, —CO$_2$H, —CO$_2$—

$C_1$–$C_4$-alkyl, $C_1$–$C_4$-perfluoroalkyl, $C_3$–$C_6$—perfluoro cycloalkyl, and 1H-tetrazol-5-yl;

$R^{4a}$ is $C_1$–$C_6$-alkyl, aryl, or —$CH_2$-aryl;

$R^5$ is H, or

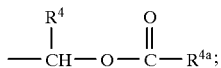

E is a single bond, —$NR^{13}(CH_2)_s$—, —$S(O)_x(CH_2)_s$— where x is 0 to 2 and s is 0 to 5, —CH(OH)—, —O—, —CO—;

$R^6$ is
(a) H,
(b) $C_1$–$C_6$-alkyl, $C_2$–$C_5$-alkenyl or $C_2$–$C_5$—alkynyl each of which can be substituted with a substituent selected from the group consisting of aryl, $C_3$–$C_7$-cycloalkyl, Cl, Br, I, F, —OH, —$CF_3$, —$CCl_3$, —$NH_2$, —NH($C_1$–$C_4$-alkyl), —N($C_1$–$C_4$-alkyl)$_2$, —NH—$SO_2R^4$, —$COOR^4$, —$SO_2NHR^9$, $C_1$–$C_4$-alkoxy, or $C_1$–$C_4$-alkyl-S,
(c) aryl;

$R^7$ is
(a) —H,
(b) $C_1$–$C_{10}$-alkyl,
(c) substituted $C_1$–$C_{10}$-alkyl in which one or more substituent(s) is selected from
  (1) I, Br, Cl, or F,
  (2) hydroxy,
  (3) $C_1$–$C_{10}$-alkoxy,
  (4) $C_1$–$C_5$-alkoxycarbonyl,
  (5) $C_1$–$C_4$-alkylcarbonyloxy,
  (6) $C_3$–$C_8$-cycloalkyl,
  (7) aryl,
  (8) heteroaryl,
  (9) $C_1$–$C_{10}$-alkyl-$S(O)_p$ in which p is 0 to 2,
  (10) $C_3$–$C_8$-cycloalkyl-$S(O)_p$,
  (11) aryl-$S(O)_p$,
  (12) oxo,
  (13) carboxy,
  (14) $NR^9R^9$,
  (15) $C_1$–$C_5$-alkylaminocarbonyl,
  (16) di($C_1$–$C_5$-alkyl)aminocarbonyl,
  (17) cyano,
  (18) —$OCONR^{22}R^{23}$,
  (19) $NR^{22}COR^{23}$,
  (20) —$NR^{22}CO_2R^{23}$,
  (21) —$NR^{22}CONR^{22}R^{23}$,
  (22) —$NR^{22}CON[CH_2CH_2]_2L$, wherein L is a single bond, $CH_2$, O, $S(O)_p$ or $NR^9$,
  (23) —$OCON[CH_2CH_2]_2L$,
(d) $C_2$–$C_{10}$-alkenyl,
(e) $C_2$–$C_{10}$-alkynyl,
(f) $C_3$–$C_8$-cycloalkyl,
(g) substituted $C_3$–$C_8$-cycloalkyl or substituted $C_3$–$C_8$-cycloalkyl-$C_1$–$C_4$-alkyl having one or more substituents selected from the group:
  (1) Cl, Br, F, or I,
  (2) hydroxy,
  (3) $C_1$–$C_6$-alkyl,
  (4) $C_1$–$C_6$-alkoxy,
  (5) $C_1$–$C_4$-alkylcarbonyloxy,
  (6) $C_1$–$C_5$-alkoxycarbonyl,
  (7) carboxy,
  (8) oxo,
  (9) $C_1$–$C_5$-alkylaminocarbonyl,
  (10) di($C_1$–$C_5$-alkyl)aminocarbonyl,
  (11) $C_1$–$C_4$-alkylcarbonyl, and
  (12) aryl,
(h) aryl, or
(i) heteroaryl, wherein heteroaryl is an unsubstituted, monosubstituted or disubstituted five or six membered aromatic ring comprising from 1 to 3 heteroatoms selected from the group consisting of O, N and S and wherein the substituents are members selected from the group consisting of —OH, —SH, $C_1$–$C_4$-alkyl, —$C_1$–$C_4$-alkoxy, —$CF_3$, Cl, Br, I, F, —$NO_2$, —$CO_2H$, —$CO_2$—$C_1$–$C_4$-alkyl, —$NH_2$, NH($C_1$–$C_4$-alkyl), —N($C_1$–$C_4$-alkyl)$_2$ and a fused benzo group;

$R^8$ is
(a) hydrogen,
(b) —OH,
(c) —$NH_2$,
(d) —NH($C_1$–$C_4$-alkyl) wherein the alkyl is unsubstituted or substituted with $CO_2R^4$,
(e) —N($C_1$–$C_4$-alkyl)$_2$ wherein one or both of the alkyl groups can be substituted with $CO_2R^4$,
(f) —$NHCO_2$—$C_1$–$C_4$-alkyl,
(g) —$NHSO_2$-aryl,
(h) —$NHSO_2$-heteroaryl,
(i) —$NHSO_2$($C_1$–$C_4$-perfluoroalkyl),
(j) —$CO_2H$,
(k) —$CO_2R^5$,
(l) Cl, Br, I, F,
(m) —$CONHSO_2$-aryl,
(n) —$CONHSO_2$-heteroaryl,
(o) —$CONHSO_2$—$C_1$–$C_4$-alkyl, either unsubstituted or substituted with aryl, —$NH_2$, —NH($C_1$–$C_4$-alkyl), —N($C_1$–$C_4$-alkyl)$_2$, —OH, —$CO_2H$, or $CO_2$ ($C_1$–$C_4$-alkyl),
(p) —$CONHSO_2$($C_1$–$C_4$-perfluoroalkyl),
(q) —$CH_2OH$,
(r) —$CH_2OCOR^4$,
(s) —O—$C_1$–$C_4$-alkyl,
(t) —$S(O)_x$—$C_1$–$C_4$-alkyl, either unsubstituted or substituted with aryl, —$NH_2$, —NH($C_1$–$C_4$-alkyl), —N($C_1$–$C_4$-alkyl)$_2$, —OH, —$CO_2H$, or $CO_2$ ($C_1$–$C_4$-alkyl),
(u) —$SO_2NHR^{21}$,
(v) —CN,
(w) tetrazol-5-yl,
(x) CONH-1-tetrazol-5-yl, or
(y) —$CH_2CO_2R^4$;

$R^9$ is H, $C_1$–$C_5$-alkyl, aryl or —$CH_2$-aryl;

$R^{10}$ is H, or $C_1$–$C_4$-alkyl;

$R_{11}$ is H, $C_1$–$C_6$-alkyl, $C_2$–$C_4$-alkenyl, $C_1$–$C_4$-alkoxy alkyl, or —$CH_2$—$C_6H_4R^{20}$;

$R^{12}$ is —CN, —$NO_2$, —$CO_2R^4$, or —$CF_3$;

$R^{13}$ is H, $C_2$–$C_4$-alkanoyl, $C_1$–$C_6$-alkyl, allyl, $C_3$–$C_6$-cycloalkyl, phenyl or benzyl;

$R^{14}$ is H, $C_1$–$C_8$-alkyl, $C_1$–$C_8$-perfluoroalkyl, $C_3$–$C_6$-cycloalkyl, phenyl or benzyl;

$R^{15}$ is H, or $C_1$–$C_6$-alkyl;

$R^{16}$ is H, $C_1$–$C_6$-alkyl, $C_3$–$C_6$-cycloalkyl, phenyl or benzyl;

$R^{17}$ is —$NR^9R^{10}$, —$OR^{10}$, —$NHCONH_2$, —$NHCSNH_2$,

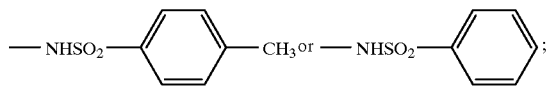

$R^{18}$ and $R^{19}$ are independently $C_1$–$C_4$-alkyl or taken together are —$(CH2)_q$— where q is 2 or 3;
$R^{20}$ is H, —$NO_2$, —$NH_2$, —OH or —$OCH_3$;
$R^{21}$ is
  (a) —CO-aryl,
  (b) —CO-$C_1$–$C_4$-alkyl,
  (c) —$COCF_3$,
  (d) —CO-heteroaryl, or
  (e) heteroaryl;
$R^{22}$ is
  (a) aryl, or
  (b) $C_1$–$C_6$-alkyl;
$R^{23}$ is
  (a) aryl,
  (b) heteroaryl,
  (c) $C_3$–$C_7$-cycloalkyl,
  (d) $C_1$–$C_8$-alkyl either unsubstituted or substituted with aryl, heteroaryl, —OH, —SH, $C_1$–$C_4$-alkyl, $C_3$–$C_7$-cycloalkyl, —O($C_1$–$C_4$-alkyl), —S($C_1$–$C_4$-alkyl), —$CF_3$, Cl, Br, I, F, —$NO_2$, —$CO_2H$, $CO_2$—$C_1$–$C_4$-alkyl, —$NH_2$, NHaryl, N(aryl)$_2$, —NH($C_1$–$C_4$-alkyl), —N($C_1$–$C_4$-alkyl)$_2$, —$NR^4CO_2R^{22}$, —$NR^4COR^{22}$, —$CONR^4R^{22}$, —O—$CONR^4R^{22}$, —$SO_2NR^4R$—$PO^{22}$, —$NR^4SO_2R^{22}$, —$PO_3H$, —PO(OH)(O—$C_1$–$C_4$-alkyl), or —N($CH_2$ $CH_2$)$_2$L wherein L is a single bond, —$CH_2$—, —O—, —S(O)$_p$, or $NR^9$, or
  (e) perfluoro-$C_1$–$C_4$-alkyl;
X is
  (a) a carbon-carbon single bond,
  (b) —CO—,
  (c) —O—,
  (d) —S—,
  (e)
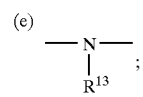
  (f)
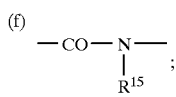
  (g)
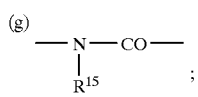
  (h) —$OCH_2$—,
  (i) —$CH_2O$—,
  (j) —$SCH_2$—,
  (k) —$CH_2S$—,
  (l) —NHC($R^9$)($R^{10}$),
  (m) —$NR^9SO_2$—,
  (n) —$SO_2NR^9$—,
  (o) —C($R^9$)($R^{10}$)NH—,
  (p) —CH=CH—,
  (q) —CF=CF—,
  (r) —CH=CF—,
  (s) —CF=CH—,
  (t) —$CH_2CH_2$—,
  (u) —$CF_2CF_2$—,
  (v)
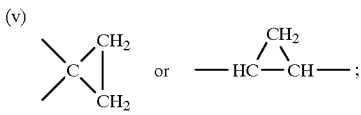
  (w)
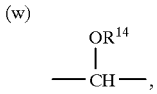
  (x)
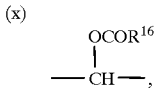
  (y)
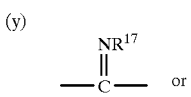
  (z)
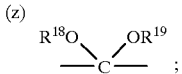

Z is O, $NR^{13}$ or S;
r is 1 or 2.

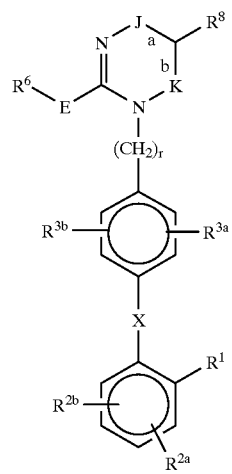
(H)

or a pharmaceutically acceptable salt thereof, wherein:
J is —C(=M)— or
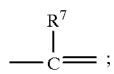

K is —C(=M)— or
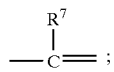

provided that one and only one of J and K is —C(=M)—;
M is O or $NR^{21}$;
one of a and b is a double bond, provided that when J is —C(=M)— b is a double bond and when K is —C(=M)— a is a double bond;

$R^1$ is
- (a) —NHSO$_2$R$^{21}$,
- (b) —NHSO$_2$NHCOR$^{21}$,
- (c) —NHCONHSO$_2$R$^{21}$,
- (d) —SO$_2$NHR$^{21}$,
- (e) —SO$_2$NHCOR$^{21}$,
- (f) —SO$_2$NHCONR$^9$R$^{21}$,
- (g) —SO$_2$NHCOOR$^{21}$,
- (h) —SO$_2$NHOR$^{21}$,
- (i) —CH$_2$SO$_2$NHCOR$^{21}$,
- (j) —CH$_2$SO$_2$NHCONHR$^{21}$,
- (k) —CO$_2$H, or
- (l) —1H-tetrazol-4-yl;

$R^{2a}$ and $R^{2b}$ are each independently
- (a) H,
- (b) Cl, Br, I, F,
- (c) CF$_3$,
- (d) C$_1$–C$_4$-alkyl, or
- (e) C$_1$–C$_4$-alkoxy;

$R^{3a}$ is
- (a) H,
- (b) Cl, Br, I, F,
- (c) C$_1$–C$_6$-alkyl,
- (d) C$_1$–C$_6$-alkoxy, or
- (e) C$_1$–C$_6$-alkoxy-C$_1$–C$_4$-alkyl;

$R^{3b}$ is
- (a) H,
- (b) Cl, Br, I, F,
- (c) C$_1$–C$_6$-alkyl, C$_2$–C$_6$-alkenyl, C$_2$–C$_6$-alkynyl,
- (d) C$_1$–C$_6$-acyloxy,
- (e) C$_3$–C$_6$-cycloalkyl,
- (f) C$_1$–C$_6$-alkoxy, or
- (g) perfluoro-C$_1$–C$_4$-alkyl;

$R^4$ is H, C$_1$–C$_6$-alkyl unsubstituted or substituted with aryl, wherein aryl is phenyl optionally substituted with one or two substituents selected from the group consisting of Cl, Br, I, F, or C$_1$–C$_4$-alkyl unsubstituted or substituted with members selected from the group consisting of N(R$^4$)$_2$, CO$_2$R$^4$, OH, N(R$^4$)CO$_2$R$^{21}$, S(O)$_x$R$^{21}$ where x is 0 to 2, C$_1$–C$_4$-alkoxy, NO$_2$, CF$_3$, C$_1$–C$_4$-alkylthio, OH, NH$_2$, —NH(C$_1$–C$_4$-alkyl), —N(C$_1$–C$_4$-alkyl)$_2$, —CO$_2$H, —CO$_2$—C$_1$–C$_4$-alkyl, —N(R$^4$)CO$_2$R$^{21}$ or 1H-tetrazol-5-yl;

$R^{4a}$ is C$_1$–C$_6$-alkyl, aryl or aryl-CH$_2$—;

E is a single bond, —NR$^{13}$(CH$_2$)$_s$—, —S(O)$_x$(CH$_2$)s— where x is 0 to 2 and s is 0 to 5, —CH(OH)—, —O—, CO—;

$R^6$ is
- (a) aryl;
- (b) C$_1$–C$_6$-alkyl, C$_2$–C$_5$-alkenyl or C$_2$–C$_5$-alkynyl each of which can be unsubstituted or substituted with a substituent selected from the group consisting of aryl, C$_3$–C$_7$-cycloalkyl, Cl, Br, I, F, —OH, CF$_3$, —CF$_2$CF$_3$, CCl$_3$, —NH$_2$, —NH(C$_1$–C$_4$-alkyl), —N(C$_1$–C$_4$-alkyl)$_2$, —NH-SO$_2$R$^4$, —COOR$^4$, —SO$_2$NHR$^9$, C$_1$–C$_4$-alkoxy, C$_1$–C$_4$-alkyl-S;
- (c) heteroaryl, wherein heteroaryl is defined as an unsubstituted, monosubstituted or disubstituted 5 or 6 membered heteroaromatic ring which can contain one or two members selected from the group consisting of N, O, S, and wherein the substituents are members selected from the group consisting of —OH, —SH, C$_1$–C$_4$-alkyl, C$_1$–C$_4$-alkyloxy, —CF$_3$, Cl, Br, I, F, NO$_2$, —CO$_2$H, —CO$_2$—C$_1$–C$_4$-alkyl, —NH$_2$, —NH(C$_1$–C$_4$-alkyl), —N(C$_1$–C$_4$-alkyl)$_2$;
- (d) C$_3$–C$_7$-cycloalkyl;

$R^7$ and $R^8$ are independently
- (a) H,
- (b) aryl-C$_1$–C$_4$-alkyl-,
- (c) heteroaryl-C$_1$–C$_4$-alkyl-,
- (d) C$_1$–C$_6$-alkyl optionally substituted with a substituent selected from the group consisting of —OH, —NH$_2$, guanidino, C$_1$–C$_4$-alkoxy, —S(O)$_x$—R$^{21}$, C$_1$–C$_4$-alkylamino, C$_1$–C$_4$-dialkylamino, —COOR$^4$, —CON(R$^4$)R$^{21}$, —OCON(R$^4$)R$^{21}$, —O—COR$^4$, C$_3$–C$_5$-cycloalkyl, —N(R$^4$)CON(R$^4$)R$^{21}$, —N(R$^4$)COOR$^{21}$, —CONHSO$_2$R$^{21}$, —N(R$^4$)SO$_2$R$^{21}$,
- (e) C$_2$–C$_4$-alkenyl,
- (f) —CO-aryl,
- (g) C$_3$–C$_7$-cycloalkyl,
- (h) Cl, Br, I, F,
- (i) —OH,
- (j) —OR$^{21}$,
- (k) perfluoro-C$_1$–C$_4$-alkyl,
- (l) —SH,
- (m) —S(O)$_x$R$^{21}$ where x is as defined above,
- (n) —CHO,
- (o) —CO$_2$R$^4$,
- (p) —SO$_3$H,
- (q) —N(R$^4$)$_2$,
- (r) —NR$^4$CO$_2$R$^{21}$,
- (s) —SO$_2$NR$^9$R$^{10}$,
- (t) —CH$_2$OCOR$^4$,
- (u) —N(R$^4$)—SO$_2$—C$_1$–C$_4$-alkyl,
- (v) 5 or 6 membered saturated heterocycle containing one nitrogen atom and optionally containing one other heteroatom selected from N, O or S, such as pyrrolidine, morpholine, or piperazine,
- (w) aryl,
- (x) heteroaryl,
- (y) 1H-tetrazol-5-yl,
- (z) —NHSO$_2$-perfluoro-C$_1$–C$_4$-alkyl,
- (aa) —CONHSO$_2$R$^{21}$,
- (bb) —SO$_2$NHCOR$^{21}$,
- (cc) —SO$_2$NH-heteroaryl,
- (dd) —S(O)$_x$-aryl,
- (ee) —S(O)$_x$CH$_2$-aryl,
- (ff) —CON(R$^4$)$_2$;

$R^9$ is H, C$_1$–C$_5$-alkyl, phenyl or benzyl;

$R^{10}$ is H, or C$_1$–C$_4$-alkyl;

$R^{11}$ is H, C$_1$–C$_6$-alkyl, C$_2$–C$_4$-alkenyl, C$_1$–C$_4$-alkoxy alkyl, or —CH$_2$—C$_6$H$_4$R$^{20}$;

$R^{12}$ is —CN, —NO$_2$ or —CO$_2$R$^4$;

$R^{13}$ is H, C$_1$–C$_4$-acyl, C$_1$–C$_6$-alkyl, allyl, C$_3$–C$_6$-cycloalkyl, phenyl or benzyl;

$R^{14}$ is H, C$_1$–C$_8$-alkyl, C$_1$–C$_8$-perfluoroalkyl, C$_3$–C$_6$-cycloalkyl, phenyl or benzyl;

$R^{15}$ is H, C$_1$–C$_6$-alkyl;

$R^{16}$ is H, C$_1$–C$_6$-alkyl, C$_3$–C$_6$-cycloalkyl, phenyl or benzyl;

$R^{17}$ is —NR$^9$R$^{10}$, —OR$^{10}$, —NHCONH$_2$, -NHCSNH$_2$,

—NHSO$_2$—⟨C$_6$H$_4$⟩—CH$_3$ or —NHSO$_2$—⟨C$_6$H$_5$⟩;

$R^{18}$ and $R^{19}$ are independently C$_1$–C$_4$-alkyl or taken together are —(CH$_2$)$_q$— where q is 2 or 3;

$R^{20}$ is H, —NO$_2$, —NH$_2$, —OH or —OCH$_3$;

$R^{21}$ is
- (a) aryl,
- (b) heteroaryl,
- (c) $C_3-C_7$-cycloalkyl,
- (d) $C_1-C_8$-alkyl wherein alkyl is unsubstituted or substituted with one or two substituents selected from the group consisting of aryl, heteroaryl, —OH, —SH, $C_1-C_4$-alkyl, —O($C_1-C_4$-alkyl), —S($C_1-C_4$-alkyl), —$CF_3$, Cl, Br, F, I, —$NO_2$, —$CO_2H$, —$CO_2$—$C_1-C_4$-alkyl, —$NH_2$, —$NR^4CO_2R^{22}$, —NH($C_1-C_4$-alkyl), —N($C_1-C_4$-alkyl)$_2$, —$PO_3H_2$, —PO(OH)(O—$C_1-C_4$-alkyl), —PO(OR$^4$)R$^9$, —$NR^4COR^{4a}$, —$CONR^4R^{4a}$, —$OCONR^4R^{4a}$, —$SO_2NR^4R^{4a}$, —$NR^4SO_2R^{4a}$, or
- (e) perfluoro-$C_1-C_4$-alkyl;

X is
- (a) a carbon-carbon single bond,
- (b) —CO—,
- (c) —O—,
- (d) —S—,
- (e) 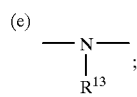
- (f) 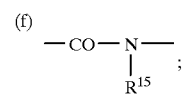
- (g) 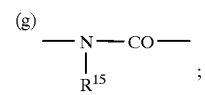
- (h) —$OCH_2$—,
- (i) —$CH_2O$—,
- (j) —$SCH_2$—,
- (k) —$CH_2S$—,
- (l) —NHC($R^9$)($R^{10}$),
- (m) —$NR^9SO_2$—,
- (n) —$SO_2NR^9$—,
- (o) —C($R^9$)($R^{10}$)NH—,
- (p) —CH=CH—,
- (q) —CF=CF—,
- (r) —CH=CF—,
- (s) —CF=CH—,
- (t) —$CH_2CH_2$—,
- (u) —$CF_2CF_2$—,
- (v) 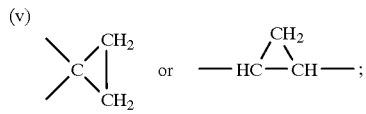
- (w) 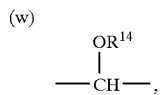
- (x) 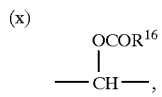
- (y) 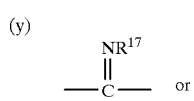

-continued
- (z) 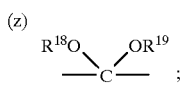

r is 1 or 2.

The compounds of formulae (I) and (I') and the processes for their preparation are described in detail in patent application EP-A-477049.

The compounds of formula (I") and the process for their preparation form the subject of patent application FR 9312136 filed on Oct. 12, 1993. The process for their preparation is now restated below.

This process for the preparation of the substituted 1-naphthylpyrazole-3-carboxamides of formula I and the salts thereof with mineral or organic bases comprises 1) treating a functional derivative of a 1-naphthylpyrazole-3-carboxylic acid of the formula

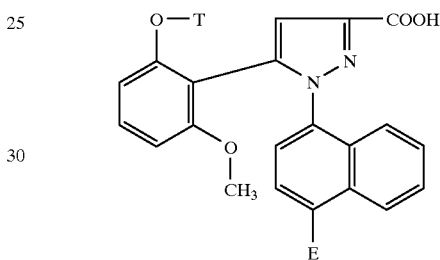

IV

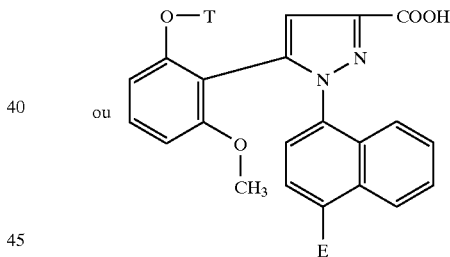

IV' in which T and E are as defined above for the compound of formula (I") and E' is a precursor of E selected from nitro, amino, hydroxyl, sulfo, chlorosulfonyl and carboxymethyl groups, with an amino acid optionally protected by the protecting groups conventionally used in peptide synthesis, of the formula

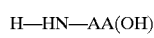   V in which —NH—AA(OH) is as defined above for the compound of formula (I");

2) if appropriate, subjecting the resulting functional derivative of the acid, of the formula

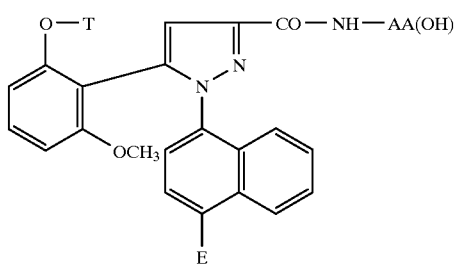

(I"a)

to a subsequent treatment appropriate for converting the substituent E', the precursor of E, to the substituent E;

3) if appropriate, deprotecting the compound thus obtained in step 1) or step 2) to give the corresponding free acid of formula (I"); and 4) if appropriate, preparing a salt of the resulting compound I.

As the functional derivative of the substituted 1-naphthylpyrazole-3-carboxylic acid of formula IV or IV', it is possible to use the acid chloride, the anhydride, a mixed anhydride, a $C_1$–$C_4$-alkyl ester, an activated ester, for example the p-nitrophenyl ester, or the free acid appropriately activated for example with N,N-dicyclohexylcarbodiimide or with benzotriazol-N-oxytris(dimethylamino)phosphonium hexafluorophosphate (BOP).

The amino acids of formula V can be used either as such or after prior protection with protecting groups conventionally used in peptide synthesis.

Thus, in step 1) of the process, the chloride of a 1-naphthylpyrazole-3-carboxylic acid, obtained by reacting thionyl chloride with an acid of formula IV or IV', can be reacted with an amino acid of formula V in a solvent such as acetonitrile, THF, DMF or DCM, under an inert atmosphere, at room temperature, for a period of between a few hours and a few days, in the presence of a base such as pyridine, sodium hydroxide or triethylamine.

One variant of step 1) consists in preparing the acid chloride or the mixed anhydride of a 1-naphthylpyrazole-3-carboxylic acid by reacting isobutyl or ethyl chloroformate with an acid of formula IV in the presence of a base such as triethylamine, and in reacting it with an N,O-bistrimethylsilyl derivative of an amino acid of formula V, obtained by reacting bis(trimethylsilyl)acetamide, 1,3-bis(trimethylsilyl)urea or bis(trifluoromethyl)acetamide with an amino acid of formula V, in solvents such as acetonitrile or DCM, under an inert atmosphere, at room temperature, for a period of between 1 day and a few days.

Another variant of the procedure of step 1) consists in reacting the mixed anhydride of a 1-naphthylpyrazole-3-carboxylic acid with an amino acid of formula V in a solvent such as DCM, under an inert atmosphere, at room temperature, for a period of between 1 day and a few days, in the presence of a base such as triethylamine.

The process for the preparation of the compounds IV or IV' via the esters IVa or IV'a is represented by the following scheme:

SCHEME 1

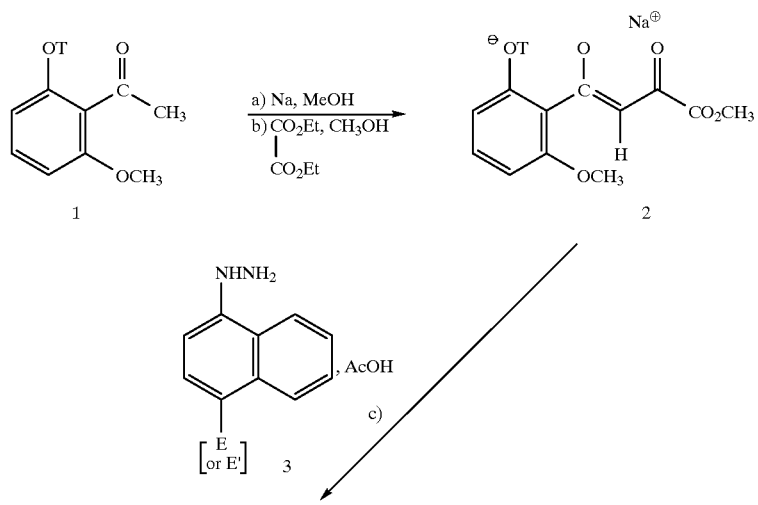

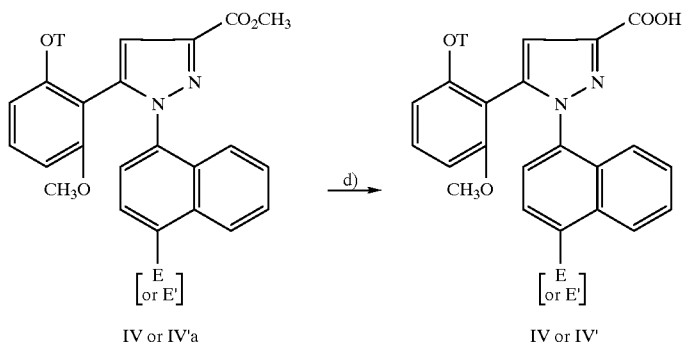

IV or IV'a      IV or IV'

In the first step, a), a strong base, such as sodium methylate, is reacted with a ketone of formula 1, in which T is as defined above, this being followed (step b)) by reaction with an equimolar amount of ethyl oxalate in an alkanol, for example methanol, according to L. Claisen, Ber., 1909, 42, 59. After precipitation in an ether such as ethyl ether or isopropyl ether, the sodium enolates 2 are filtered off. It is also possible to prepare a lithium enolate according to W. V. Murray et al., J. Heterocyclic Chem., 1989, 26, 1389.

The metal enolate 2 prepared in this way is then refluxed with an excess of the naphthylhydrazine derivative 3, or a salt thereof, in acetic acid (step c)) to give the esters IVa or IV'a.

Saponification of the esters IVa or IV'a by reaction with an alkaline agent, for example potassium hydroxide or sodium hydroxide, followed by acidification, gives the acids IV or IV' (step d)).

If the product of formula (I'') has a basic group and is obtained in the form of the free base, salification is effected by treatment with the chosen acid in an organic solvent. Treatment of the free base, dissolved for example in an alcohol such as isopropanol, with a solution of the chosen acid in the same solvent gives the corresponding salt, which is isolated by the conventional techniques. The hydrochloride, hydrobromide, sulfate, hydrogensulfate, dihydrogenphosphate, methanesulfonate, methylsulfate, oxalate, maleate, fumarate and naphthalene-2-sulfonate, for example, are prepared in this way.

If the compound of formula (I'') has a basic group and is isolated in the form of one of its salts, for example the hydrochloride or oxalate, the free base can be prepared by neutralizing said salt with a mineral or organic base such as sodium hydroxide or triethylamine, or with an alkali metal carbonate or bicarbonate such as sodium or potassium carbonate or bicarbonate.

If the product of formula (I'') is obtained in the acid form, it can be converted to a metal salt, especially an alkali metal salt such as the sodium salt, or an alkaline earth metal salt such as the calcium salt, by the conventional processes.

The naphthylhydrazine derivatives carrying a substituent E or a substituent E' can be prepared by diazotizing the corresponding naphthylamine in the presence of sodium nitrite and then reducing the diazonium salt, for example by reaction with stannous chloride. The substituted naphthylamines are known or are prepared by known methods.

The conversion of a compound of formula (I''a) or formula IV' in which the naphthyl group is substituted by E' to a compound of formula I'' or, respectively, formula IV in which the naphthyl group is substituted by E is effected by conventional methods well known to those skilled in the art.

For example, if E'=$SO_3H$, a compound IV' in which E'=$SO_2Cl$ is prepared and this is then converted to another compound, IV, in which E is an optionally substituted aminosulfonyl group by reaction with an appropriate amine of the formula $NHG_1G_2$, $HN(E_1)(CH_2)_n$—$NE'_1E'_2$ or, respectively,

in which $E_1$, $E_2$, $E'_1$, $E'_2$ and n are as defined above for the compound of formula (I'').

The compounds of formula IV' or (I''a) in which E' is a carboxymethyl group are useful for the preparation of the compounds IV or, respectively, I'' in which E is a carbamoylmethyl group in which the nitrogen atom is free or substituted.

The compounds of formula IV' or the compounds of formula I''a in which E' is a nitro group can be converted to compounds of formula IV' or, respectively, formula I''a in which E' is an amino group, after which the compounds of formula IV or, respectively, formula I'' in which E is a nitrogen atom variously substituted by an acyl group or by a sulfonyl group, as defined above for the compounds of formula I'', are prepared by known methods. It is also possible to prepare compounds IV' or I''a in which E' is a hydroxyl from compounds in which E' is an amino. The latter compounds make it possible to prepare compounds IV or, respectively, I'' in which the substituent E is a variously substituted oxygen, as defined above for the compounds I''.

The compounds of formula IV or the compounds of formula I'' in which E is a cyano group make it possible to prepare the compounds IV or, respectively, the compounds I'' in which E is a carbamoyl group which is free or substituted on the nitrogen, as defined above for I''. Likewise, the compounds of formula IV or I' in which E=CN can be converted to compounds of formula IV or, respectively, I'' in which E is $(NH_2)C$=$NOH$ or E is $CH_2NHCOR_3$.

The amino acids not available commercially are prepared by the synthesis of Strecker, Ann., 1850, 75, 27, or by the synthesis of H. T. Bucherer et al., J. Pract. Chem., 1934, 141, 5, followed by hydrolysis to give the amino acids; for example, 2-aminoadamantane-2-carboxylic acid is prepared according to H. T. Nagasawa et al., J. Med. Chem., 1973, 16, (7), 823.

α-Amino-1-adamantylacetic and α-amino-2-adamantylacetic acids are prepared according to B. Gaspert et al., Croatico Chemica Acta, 1976, 48, (2), 169–178.

2-Aminonorbornane-2-carboxylic acid is prepared according to H. S. Tager et al., J. Am. Chem. Soc., 1972, 94, 968.

The α-aminocycloalkylcarboxylic acids are prepared according to J. W. Tsang et al., J. Med. Chem., 35 1984, 27, 1663.

The R- and S-cyclopentylglycines are prepared according to European patent application EP-477049.

The R- and S-cyclohexylglycines are prepared according to Rudman et al., J. Am. Chem. Soc., 1952, 74, 551.

The R- and S-cyclohexylglycines can also be prepared by catalytic hydrogenation of the R- and S-phenylglycines.

The α-aminocycloalkylcarboxylic acids of R or S configuration can also be prepared by stereospecific enzymatic hydrolysis of the corresponding racemic N-acetyl derivatives according to J. Hill et al., J. Org. Chem., 1965, 1321.

The diuretic activity according to the present invention was demonstrated by intracerebroventricular, subcutaneous and oral administration with the aid of a test on rats which were watered and fed normally; the method used is described below.

Method

Male rats (Crl:CD® BR—Charles River Italia) weighing 220±30 g are kept under standard conditions in groups of 4 in plastic cages with a wire mesh floor (illumination for one day from 6.30 am to 6.30 pm, temperature 22±1°C., humidity 55±15%) and are fed and watered normally. On the day of the experiment, 1 hour prior to administration of the test product, the animals are placed in metabolic cages without food or water. After administration of the test product, the urine excretion is evaluated for 3 to 6 hours, depending on the chosen method of administration. The test product is administered orally (p.o.) in 0.5% carboxymethyl cellulose and subcutaneously (s.c.) and intracerebroventricularly (i.c.v.) in 4% propylene glycol, pH 7.4. The controls receive only the vehicle (2 ml/kg s.c. or p.o., 10 μl/rat i.c.v.). The compounds tested n this experiment, at doses of 0.5 to 20 mg/kg p.o., 0.03 to 3 mg/kg i.p., 0.5 mg/kg s.c. and 0.1 and 1 μg/rat i.c.v., cause a large increase in urine excretion in the treated animals, which is 3 to 10 times greater than in the controls.

Through the discovery of this activity, neurotensin antagonists can be used for the preparation of diuretic drugs indicated in the treatment of edematous states of different origins, for example renal insufficiency, nephrotic syndrome, congestive cardiac insufficiency, acute pulmonary edema, cerebral edema, cirrhoses associated with ascites, and acute renal insufficiency induced as a side-effect by certain drugs such as cisplatin and gentamicin. The compounds according to the present invention can optionally be used in association with other diuretics acting by different mechanisms.

For their use as drugs according to the invention, the neurotensin antagonists must be formulated as pharmaceutical compositions.

In the pharmaceutical compositions of the present invention for oral, sublingual, subcutaneous, intramuscular, intravenous, topical, transdermal or rectal administration, the active principle can be administered to animals and humans in the form of unit doses, as a mixture with conventional pharmaceutical carriers, for the treatment of the abovementioned complaints. The appropriate unit doses include doses for oral administration, such as tablets, which may be divisible, gelatin capsules, powders, granules and oral solutions or suspensions, doses for sublingual and buccal administration, doses for subcutaneous, intramuscular or intravenous administration and doses for rectal administration.

If a solid composition is prepared in the form of tablets, the main active ingredient is mixed with a pharmaceutical vehicle such as gelatin, starch, lactose, magnesium stearate, talc, gum arabic or the like. The tablets can be coated with sucrose or other appropriate substances or else they can be treated so as to have a sustained or delayed activity and so as to release a predetermined amount of active principle continuously.

A gelatin capsule preparation is obtained by mixing the active ingredient with a diluent and pouring the resulting mixture into soft or hard gelatin capsules.

A preparation in the form of a syrup or elixir can contain the active ingredient together with a sweetener, which is preferably calorie-free, methylparaben and propylparaben as antiseptics, a flavoring and an appropriate color.

The water-dispersible powders or granules can contain the active ingredient mixed with dispersants, wetting agents or suspending agents such as polyvinylpyrrolidone, as well as with sweeteners or taste correctors.

Rectal administration is effected using suppositories which are prepared with binders melting at the rectal temperature, for example cocoa butter or polyethylene glycols.

Parenteral administration is effected using aqueous suspensions, saline solutions or sterile and injectable solutions which contain pharmacologically compatible dispersants and/or wetting agents, for example propylene glycol or butylene glycol.

The active principle can also be formulated as microcapsules, optionally with one or more carriers or additives.

In the pharmaceutical compositions according to the present invention, the active principle can also be in the form of an inclusion complex in cyclodextrins or ethers or esters thereof.

To obtain the diuretic effect, the dose of active principle can vary between 1 and 1000 mg per day, preferably between 10 and 500 mg, depending on the weight and age of the patient and the severity of the complaints to be treated.

Each unit dose can contain from 1 to 500 mg of active principle, preferably from 10 to 250 mg; this unit dose can be administered 1 to 4 times a day.

For their diuretic action, neurotensin antagonists can also be used for the preparation of drugs with an antihypertensive action, either by themselves or in association with other active principles. More particularly, according to the present invention, neurotensin antagonists, especially the compounds of formulae I, I', I", II and III, can be associated with a calcium antagonist, a β-blocker which is preferably $\beta_1$-selective, or a converting enzyme inhibitor.

The following Example illustrates the invention.

EXAMPLE 1

The diuretic activity of a representative compound of the invention (SR 48692) was determined by the method described above.

The results of the experiments are shown in Tables I and II below.

TABLE I

| | Dose | CUMULATIVE URINE EXCRETION (ml/rat) | | |
|---|---|---|---|---|
| | μg/rat | 1h[a] | 2h | 3h |
| Controls | — | 0.24 ± 0.06 | 0.54 ± 0.14 | 2.64 ± 0.19 |
| SR 48692 | 0.1 | 0.70 ± 0.11 * | 2.48 ± 0.35 ** | 5.97 ± 0.50 * |
| | 1 | 2.80 ± 0.19 ** | 4.47 ± 0.28 ** | 7.98 ± 0.46 ** |

The data are the mean ± SEM for 3 to 7 rats.
SR 48692 in a volume of 10 μl/rat is administered i.c.v.
[a] as from administration
*, ** $p < 0.05, 0.01$ compared with the controls (Duncan test)

TABLE II

| Dose | CUMULATIVE URINE EXCRETION (ml/rat) | | |
|---|---|---|---|
| μg/rat | 1h[a] | 3h | 5h |
| Controls — | 0 | 0.83 ± 0.13 | 1.17 ± 0.50 |
| SR 48692  0.5 | 1.44 ± 0.20** | 4.14 ± 0.74** | 5.60 ± 0.65** |

The data are the mean ± SEM for at least 12 rats.
SR 48692 in a volume of 2 ml/kg is administered subcutaneously.
[a] as from administration
**p < 0.01 compared with the controls (Duncan test)

In these experiments, the compound SR 48692 showed a very substantial diuretic activity, which manifests itself not only after subcutaneous administration (Table II) but also after intracerebroventricular, i.e. central, administration (Table I).

It has further been proven that the compound SR 48692 is also active after oral administration and that its effects are dose-dependent; at doses ranging from 0.5 to 20 mg/kg, SR 48692 exerts a strong diuretic activity, increasing the urine excretion by a factor of 3 to 10 compared with the controls (evaluation performed over 6 hours).

What is claimed is:

1. A method for the treatment of an edematous state in a human or non-human animal subject which is not caused by administering neurotensin to said subject, comprising administering to said subject an effective amount of a neurotensin antagonist having diuretic activity; wherein said neurotensin antagonist is a compound of formula (II):

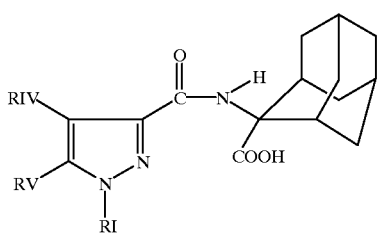

(II)

Or a pharmaceutically acceptable salt or solvate thereof;
in which
RI is
group

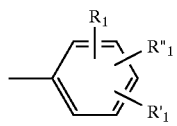

where $R_1$, $R'_1$ and $R''_1$ are each independently a hydrogen atom, a halogen atom, a hydroxyl, a linear or branched $C_1$–$C_4$-alkyl group, a $C_1$–$C_4$-alkoxy group, a trifluoromethyl group, a trifluoromethoxy group, a nitro group, a carboxyl group or an amino group;
a carboxyalkyl or alkoxycarbonylalkyl group in which the alkyls are $C_1$–$C_4$;
a cycloalkyl group in which the alkyls are $C_3$–$C_6$;
a tetrahydronaphthyl group;
a pyridyl group;
a naphthyl substituted by $R_1$, $R'_1$ and $R''_1$ as defined above;
a benzyl group substituted by $R_1$, $R'_1$ and $R''_1$ as defined above;
a cinnamyl group optionally substituted on the aromatic ring by a halogen, a hydroxyl or a $C_1$–$C_4$-alkoxy;
a quinolyl or isoquinolyl group optionally substituted by $R_1$, $R'_1$ and $R''_1$ as defined above;
a benzothiazol-2-yl group;
a quinoxalinyldione group;
a phthalazin-1-yl group;
a benzothiadiazolyl group; or
a methylene group substituted by a 5- or 6-membered heterocyclic grouping such as, in particular, a pyridyl and a thienyl;

RIV is a hydrogen atom, a halogen atom or a $C_1$–$C_6$-alkyl;
RV is
a group

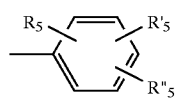

where $R_5$, $R'_5$ and $R''_5$ are each independently a hydrogen atom, a halogen atom, a linear or branched $C_1$–$C_4$-alkyl, a hydroxyl, a $C_1$–$C_4$-alkoxy, a nitro, a trifluoromethyl, a trifluoromethoxy, a cyano, an amino, a carboxyl, a $C_1$–$C_4$-carboxyalkyl or a phenyl;
a naphthyl group which is unsubstituted or substituted by a $C_1$–$C_4$-alkyl;
a pyridyl group; or
a styryl group which is unsubstituted or substituted by a $C_1$–$C_4$-alkyl;
or RIV and RV, taken together, are a group

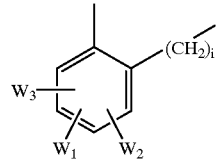

in which the phenyl group substitutes the pyrazole in the 5-position and the group —$(CH_2)_i$—, in which i=1 to 3, substitutes the pyrazole in the 4-position, and $W_1$, $W_2$ and $W_3$ substitute the benzene ring and are independently hydrogen, a halogen or a hydroxyl group.

2. A method for the treatment of an edematous state in a human or non-human animal subject which is not caused by administering neurotensin to said subject, comprising administering to said subject an effective amount of a neurotensin antagonist having diuretic activity; wherein said neurotensin antagonist is 2-{[1-(7-chloroquinolin-4-yl)-5-(2,6-dimethoxyphenyl)-1H-pyrazole-3-carbonyl]amino}adamantane-2-carboxylic acid or a pharmaceutically acceptable salt or solvate thereof.

* * * * *